United States Patent [19]
Raymond et al.

[11] Patent Number: 6,153,424
[45] Date of Patent: Nov. 28, 2000

[54] **PROTEASE-DEFICIENT STRAINS OF *PICHIA METHANOLICA***

[75] Inventors: Christopher K. Raymond; Erica Vanaja, both of Seattle, Wash.

[73] Assignee: ZymoGenetics, Inc., Seattle, Wash.

[21] Appl. No.: 09/265,628

[22] Filed: Mar. 9, 1999

Related U.S. Application Data

[63] Continuation-in-part of application No. 09/152,180, Sep. 11, 1998, and a continuation of application No. 08/703,807, Aug. 26, 1996.
[60] Provisional application No. 60/058,822, Sep. 15, 1997, provisional application No. 60/042,910, Jul. 17, 1996, and provisional application No. 60/006,397, Nov. 9, 1995.

[51] Int. Cl.[7] ................................................. C12N 1/14
[52] U.S. Cl. .................. 435/254.23; 435/254.23; 435/70.01; 435/219; 435/69.1; 435/6; 536/23.74; 536/24.1; 935/28; 935/37; 935/69
[58] Field of Search ................... 435/219, 69.1, 435/254.3, 69.9, 70.1, 172.3, 254.2, 255.5; 536/23.74, 24.1; 935/28, 37, 69

[56] References Cited

U.S. PATENT DOCUMENTS

| | | | |
|---|---|---|---|
| 5,324,660 | 6/1994 | Gleeson et al. | 435/254.23 |
| 5,541,112 | 7/1996 | Gleeson et al. | 435/254.23 |
| 5,792,850 | 8/1998 | Baumgartner | 536/23.5 |

FOREIGN PATENT DOCUMENTS

| | | | |
|---|---|---|---|
| WO 9217595 | 10/1992 | WIPO | 536/23.5 |
| 97/17450 | 5/1997 | WIPO . | |

OTHER PUBLICATIONS

Raymond et al., *Yeast* 14:11–23, 1998.

*Primary Examiner*—Kenneth R. Horlick
*Assistant Examiner*—Janell E. Taylor
*Attorney, Agent, or Firm*—Gary E. Parker

[57] ABSTRACT

Protease-deficient strains of the methylotrophic yeast *Pichia methanolica* and materials and methods for generating such strains are disclosed. The strains have a functional deficiency in a vacuolar protease, such as proteinase A or proteinase B. The strains are useful as hosts for the expression of heterologous genes encoding proteins of commercial or other interest.

31 Claims, 4 Drawing Sheets

SEQUENCE LISTING

<160> NUMBER OF SEQ ID NOS: 23

<210> SEQ ID NO 1
<211> LENGTH: 3077
<212> TYPE: DNA
<213> ORGANISM: Pichia methanolica

<400> SEQUENCE: 1

```
cagctgctct gctccttgat tcgtaattaa tgttatcctt ttactttgaa ctcttgtcgg      60
tccccaacag ggattccaat cggtgctcag cgggatttcc catgaggttt ttgacaactt     120
tattgatgct gcaaaaactt ttttagccgg gtttaagtaa ctgggcaata tttccaaagg     180
ctgtgggcgt tccacactcc ttgcttttca taatctctgt gtattgtttt attcgcattt     240
tgattctctt attaccagtt atgtagaaag atcggcaaac aaaatatcaa cttttatctt     300
gaacgctgac ccacggtttc aaataactat cagaactcta tagctatagg ggaagtttac     360
tgcttgctta aagcggctaa aaagtgtttg gcaaattaaa aaagctgtga caagtaggaa     420
ctcctgtaaa gggccgattc gacttcgaaa gagcctaaaa acagtgacta ttggtgacgg     480
aaaattgcta aaggagtact agggctgtag taataaataa tggaacagtg gtacaacaat     540
aaaagaatga cgctgtatgt cgtagcctgc acgagtagct cagtggtaga gcagcagatt     600
gcaaatctgt tggtcaccgg ttcgatccgg tctcgggctt ccttttttgc tttttcgata     660
tttgcgggta ggaagcaagg tctagttttc gtcgtttcgg atggtttacg aaagtatcag     720
ccatgagtgt ttccctctgg ctacctaata tatttattga tcggtctctc atgtgaatgt     780
ttctttccaa gttcggcttt cagctcgtaa atgtgcaaga aatatttgac tccagcgacc     840
tttcagagtc aaattaattt tcgctaacaa tttgtgtttt tctggagaaa cctaaagatt     900
taactgataa gtcgaatcaa catctttaaa tcctttagtt aagatctctg cagcggccag     960
tattaaccaa tagcatattc acaggcatca catcggaaca ttcagaatgg actcgcaaac    1020
tgtcgggatt ttaggtggtg gccaacttgg tcgtatgatc gttgaagctg cacacagatt    1080
```

-continued

```
gaatatcaaa actgtgattc tcgaaaatgg agaccaggct ccagcaaagc aaatcaacgc      1140
tttagatgac catattgacg gctcattcaa tgatccaaaa gcaattgccg aattggctgc      1200
caagtgtgat gttttaaccg ttgagattga acatgttgac actgatgcgt tggttgaagt      1260
tcaaaaggca actggcatca aaatcttccc atcaccagaa actatttcat tgatcaaaga      1320
taaatacttg caaaagagc atttgattaa gaatggcatt gctgttgccg aatcttgtag       1380
tgttgaaagt agcgcagcat ctttagaaga agttggtgcc aaatacggct tcccatacat      1440
gctaaaatct gaacaatgg cctatgacgg aagaggtaat tttgttgtca agacaagtc        1500 atatatacct gaagctttga agtttagaa tgacaggccg ttatacgccg agaaatgggc       1560
tccattttca aaggagttag ctgttatggt tgtgagatca atcgatggcc aagtttattc      1620
ctacccaact gttgaaacca tccaccaaaa caacatctgt cacactgtct ttgctccagc      1680
tagagttaac gatactgtcc aaaagaaggc ccaaattttg gctgacaacg ctgtcaaatc      1740
tttcccaggt gctggtatct ttggtgttga atgtttttta ttacaaaatg gtgacttatt      1800
agtcaacgaa attgccccaa gacctcacaa ttctggtcac tataccatcg acgcttgtgt      1860
cacctcgcaa tttgaagctc atgttagggc cattactggt ctacccatgc cgaagaactt      1920 cacttgttg tcgactccat ctacccaagc tattatgttg aacgttttag gtggcgatga       1980
gcaaaacggt gagttcaaga tgtgtaaaag agcactagaa actcctcatg cttctgttta      2040
cttatacggt aagactacaa gaccaggcag aaaaatgggt cacattaata tagtttctca      2100
atcaatgact gactgtgagc gtagattaca ttacatagaa ggtacgacta acagcatccc      2160
tctcgaagaa cagtacacta cagattccat tccgggcact tcaagcaagc cattagtcgg      2220
tgtcatcatg ggttccgatt cggacctacc agtcatgtct ctaggttgta atatattgaa      2280
gcaatttaac gttccattg aagtcactat cgtttccgct catagaaccc cacaaagaat       2340
ggccaagtat gccattgatg ctccaaagag agggttgaag tgcatcattg ctggtgctgg      2400
tggtgccgct catttaccgg gaatggttgc ggcgatgacg ccgctgcctg ttattggtgt      2460
ccctgttaaa ggctctactt tggatggtgt tgattcacta cactccatcg ttcaaatgcc      2520
aagaggtatt cctgttgcta ctgtggctat taacaatgct actaacgctg ccttgctagc      2580
tatcacaatc ttaggtgccg gcgatccaaa tacttgtctg caatggaagt ttatatgaac      2640
aatatggaaa atgaagtttt gggcaaggct gaaaaattgg aaaatggtgg atatgaagaa      2700
tacttgagta catacaagaa gtagaacctt ttatatttga tatagtactt actcaaagtc      2760
ttaattgttc taactgttaa tttctgcttt gcatttctga aaagtttaag acaagaaatc      2820
ttgaaatttc tagttgctcg taagaggaaa cttgcattca aataacatta acaataaatg      2880
acaataatat attatttcaa cactgctata tggtagtttt ataggtttgg ttaggatttg      2940
agatattgct agcgcttatc attatcctta attgttcatc gacgcaaatc gacgcatttc      3000
cacaaaaatt ttccgaacct gtttttcact tctccagatc ttggtttagt atagcttttg      3060
acacctaata cctgcag                                                    3077
```

<210> SEQ ID NO 2
<211> LENGTH: 3386
<212> TYPE: DNA
<213> ORGANISM: Pichia methanolica

<400> SEQUENCE: 2

```
gaattcctgc agcccggggg atcgggtagt ggaatgcacg gttatacccca ctccaaataa     60 aagtgtagta gccggactga aaggttttag gagtctgttt gtttgttcat gtgcatcatt      120
```

-continued

```
ccctaatctg ttaacagtct cggagtatac aaaaaagtaa gtcaaatatc aaggtggccg      180
ggggcagcat cgagactcga gatggtacat acttaaaagc tgccatattg aggaacttca      240 aagtttatc tgttttaga attaaaagac gattgttgta acaaaacgtt gtgcctacat        300
aaactcaaat taatggaaat agcctgtttt gaaaaataca ccttcttaag tactgacaaa      360
gttttgttaa atgactatcg aacaagccat gaaatagcac atttctgcca gtcacttta      420 acactttcct gcttgctggt tgactctcct catacaaaca cccaaaaggg aaactttcag      480 tgtgggaca cttgacatct cacatgcacc ccagattaat ttccccagac gatgcggaga       540
caagacaaaa caaccctttg tcctgctctt ttctttctca caccgcgtgg gtgtgtgcgc      600
aggcaggcag gcaggcagcg ggctgcctgc catctctaat cgctgctcct cccccctggc      660
ttcaaataac agcctgctgc tatctgtgac cagattggga caccccctc ccctccgaat       720 gatccatcac cttttgtcgt actccgacaa tgatccttcc ctgtcatctt ctggcaatca      780
gctccttcaa taattaaatc aaataagcat aaatagtaaa atcgcataca aacgtcatga      840
aaagttttat ctctatggcc aacgatagt ctatctgctt aattccatcc actttgggaa       900
ccgctctctc tttaccccag attctcaaag ctaatatctg ccccttgtct attgtccttt      960
ctccgtgtac aagcggagct tttgcctccc atcctcttgc tttgtttcgg ttattttttt     1020
ttcttttgaa actcttggtc aaatcaaatc aaacaaaacc aaaccttcta ttccatcaga     1080
tcaaccttgt tcaacattct ataaatcgat ataaatataa ccttatccct cccttgtttt     1140
ttaccaatta atcaatcttc aaatttcaaa tattttctac ttgctttatt actcagtatt     1200
aacatttgtt taaaccaact ataacttta actggcttta gaagttttat ttaacatcag      1260
tttcaattta catctttatt tattaacgaa atctttacga attaactcaa tcaaaacttt     1320
tacgaaaaaa aaatcttact attaatttct caaaatggct attccagatg aatttgatat     1380
tattgttgtc ggtggtggtt ccaccggttg tgctcttgct ggtagattag gtaacttgga     1440
cgaaaacgtc acagttgctt taatcgaagg tggtgaaaac aacatcaaca cccatgggt     1500 ttacttacca ggtgtttatc caagaaacat gagattagac tcaaagactg ctacttttta    1560
ctcttcaaga ccatcaccac acttgaacgg tagaagagct attgttccat gtgctaacat     1620
cttgggtggt ggttcttcca tcaacttctt gatgtacacc agagcctctg cctccgatta     1680
cgatgattgg gaatctgaag gttggactac cgatgaatta ttaccactaa tgaagaagat     1740
tgaaacttat caaagaccat gtaacaacag agaattgcac ggtttcgatg gtccaattaa     1800
ggtttcattt ggtaactata cttatccaaa cggtcaagat ttcattagag ctgccgaatc     1860
tcaaggtatt ccatttgttg atgatgctga agatttgaaa tgttcccacg gtgctgagca     1920
ctggttgaag tggatcaaca gagacttagg tagaagatcc gattctgctc atgcttacat     1980
tcacccaacc atgagaaaca agcaaaactt gttcttgatt acttccacca gtgtgaaaa      2040 gattatcatt gaaacggtg ttgctactgg tgttaagact gttccaatga agccaactgg      2100
ttctccaaag acccaagttg ctagaacttt caaggctaga aagcaaatta ttgtttcttg     2160
tggtactatc tcatcaccat tagttttgca aagatctggt atcggttccg ctcacaagtt     2220
gagacaagtt ggtattaaac caattgttga cttaccaggt gttggtatga acttccaaga     2280
tcactactgt ttcttcactc cataccatgt caagccagat actccatcat cgatgactt      2340 tgttagaggt gataaagctg ttcaaaaatc tgctttcgac caatggtatg ctaacaagga     2400
tggtccatta accactaatg gtattgaggc aggtgttaag attagaccaa ctgaagaaga     2460
```

```
attagccact gctgatgacg aattcagagc tgcttatgat gactactttg gtaacaagcc    2520
agataagcca ttaatgcact actctctaat ttctggtttc tttggtgacc acaccaagat    2580
tccaaacggt aagtacatgt gcatgttcca cttcttggaa tatccattct ccagaggttt    2640
cgttcacgtt gtttctccaa acccatacga tgctcctgac tttgatccag gtttcatgaa    2700
cgatccaaga gatatgtggc caatggtttg gtcttacaag aagtccagag aaactgccag    2760
aagaatggac tgttttgccg gtgaagttac ttctcaccac ccacactacc catacgactc    2820
accagccaga gctgctgaca tggacttgga aactactaaa gcttatgctg gtccagacca    2880
ctttactgct aacttgtacc acggttcatg gactgttcca attgaaaagc caactccaaa    2940
gaacgctgct cacgttactt ctaaccaagt tgaaaaacat cgtgacatcg aatacaccaa    3000
ggaggatgat gctgctatcg aagattacat cagagaacac actgaaacca catggcattg    3060
tcttggtact tgttcaatgg ctccaagaga aggttctaag gttgtcccaa ctggtggtgt    3120
tgttgactcc agattaaacg tttacggtgt tgaaaagttg aaggttgctg atttatcaat    3180
ttgcccagat aatgttggtt gtaacactta ctctactgct ttgttaatcg gtgaaaaggc    3240
ttctacctta gttgctgaag acttgggcta ctctggtgat gctttgaaga tgactgttcc    3300
aaacttcaaa ttgggtactt atgaagaagc tggtctagct agattctagg gctgcctgtt    3360
tggatatttt tataattttt gagagt                                         3386

<210> SEQ ID NO 3
<211> LENGTH: 38
<212> TYPE: DNA
<213> ORGANISM: Artificial Sequence
<220> FEATURE:
<223> OTHER INFORMATION: Oligonucleotide primer

<400> SEQUENCE: 3
tgatcaccta ggactagtga caagtaggaa ctcctgta                             38

<210> SEQ ID NO 4
<211> LENGTH: 39
<212> TYPE: DNA
<213> ORGANISM: Artificial Sequence
<220> FEATURE:
<223> OTHER INFORMATION: Oligonucleotide primer

<400> SEQUENCE: 4
cagctgccta ggactagttt cctcttacga gcaactaga                            39

<210> SEQ ID NO 5
<211> LENGTH: 17
<212> TYPE: DNA
<213> ORGANISM: Artificial Sequence
<220> FEATURE:
<223> OTHER INFORMATION: Oligonucleotide primer

<400> SEQUENCE: 5
tggttgaagt ggatcaa                                                    17

<210> SEQ ID NO 6
<211> LENGTH: 17
<212> TYPE: DNA
<213> ORGANISM: Artificial Sequence
<220> FEATURE:
<223> OTHER INFORMATION: Oligonucleotide primer

<400> SEQUENCE: 6
gtgtggtcac cgaagaa                                                    17
```

```
<210> SEQ ID NO 7
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 7
gttgttcctt ccaaaccatt gaac                                      24

<210> SEQ ID NO 8
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 8
aaagtaagaa gcgtagccta gttg                                      24

<210> SEQ ID NO 9
<211> LENGTH: 329
<212> TYPE: DNA
<213> ORGANISM: Pichia methanolica

<400> SEQUENCE: 9
gaccatgatt acgccaagcg cgcaattaac cctcactaaa gggaacaaaa gctgggtacc   60 gggcccccccc tcgaggtcga cggtatcgat aagctttatt ataacattaa tatactattt  120
tataacagga ttgaaaatta tatttatcta tctaaaacta aaattcaaaa tggctattcc  180
tgaagaattc gatatcattg ttgtcggtgg tggttctgcc ggctgtccta ctgctggtag  240
attggctaac ttagacccaa atttaactgt tgctttaatc gaagctggtg aaaacaacat  300
taacaaccca tgggtctact taccaggcg                                   329

<210> SEQ ID NO 10
<211> LENGTH: 17
<212> TYPE: DNA
<213> ORGANISM: Artificial Sequence
<220> FEATURE:
<223> OTHER INFORMATION: Oligonucleotide primer

<400> SEQUENCE: 10
acctcccagt aagcctt                                              17

<210> SEQ ID NO 11
<211> LENGTH: 17
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)...(17)
<223> OTHER INFORMATION: n = A,T,C or G

<400> SEQUENCE: 11
ttyggnaart tygaygg                                              17

<210> SEQ ID NO 12
<211> LENGTH: 421
<212> TYPE: DNA
<213> ORGANISM: Pichia methanolica
<220> FEATURE:
```

<221> NAME/KEY: CDS
<222> LOCATION: (2)...(421)

<400> SEQUENCE: 12

```
g gaa ggt aac gtt tct cag gat act tta gct tta ggt gat tta gtt att         49
  Glu Gly Asn Val Ser Gln Asp Thr Leu Ala Leu Gly Asp Leu Val Ile
   1               5                  10                  15 cca aaa caa gac ttt gcc gaa gct act tct gag cca ggt tta gca ttc           97
Pro Lys Gln Asp Phe Ala Glu Ala Thr Ser Glu Pro Gly Leu Ala Phe
             20                  25                  30 gca ttt ggt aaa ttt gat ggt att tta ggt tta gct tac gat agc att         145
Ala Phe Gly Lys Phe Asp Gly Ile Leu Gly Leu Ala Tyr Asp Ser Ile
         35                  40                  45 tcg gtc aac aag att gtt cct cct att tat aat gct tta aac ttg ggt         193
Ser Val Asn Lys Ile Val Pro Pro Ile Tyr Asn Ala Leu Asn Leu Gly
     50                  55                  60 tta tta gat gaa cct caa ttt gcc ttc tac cta ggt gat act aac acc         241
Leu Leu Asp Glu Pro Gln Phe Ala Phe Tyr Leu Gly Asp Thr Asn Thr
 65                  70                  75                  80 aat gaa gaa gat ggt ggt ctt gcc act ttt ggt ggt gtt gat gag tcc         289
Asn Glu Glu Asp Gly Gly Leu Ala Thr Phe Gly Gly Val Asp Glu Ser
                 85                  90                  95 aag tat act ggt aaa gtt aca tgg tta cca gtc aga aga aag gct tac         337
Lys Tyr Thr Gly Lys Val Thr Trp Leu Pro Val Arg Arg Lys Ala Tyr
            100                 105                 110 tgg gaa gtt tca tta gac ggt att tca tta ggt gat gaa tac gcg cca         385
Trp Glu Val Ser Leu Asp Gly Ile Ser Leu Gly Asp Glu Tyr Ala Pro
        115                 120                 125 tta gaa ggc cat gga gct gcc att gat aca ggt acc                         421
Leu Glu Gly His Gly Ala Ala Ile Asp Thr Gly Thr
    130                 135                 140
```

<210> SEQ ID NO 13
<211> LENGTH: 140
<212> TYPE: PRT
<213> ORGANISM: Pichia methanolica

<400> SEQUENCE: 13

```
Glu Gly Asn Val Ser Gln Asp Thr Leu Ala Leu Gly Asp Leu Val Ile
 1               5                  10                  15

Pro Lys Gln Asp Phe Ala Glu Ala Thr Ser Glu Pro Gly Leu Ala Phe
             20                  25                  30

Ala Phe Gly Lys Phe Asp Gly Ile Leu Gly Leu Ala Tyr Asp Ser Ile
         35                  40                  45

Ser Val Asn Lys Ile Val Pro Pro Ile Tyr Asn Ala Leu Asn Leu Gly
     50                  55                  60

Leu Leu Asp Glu Pro Gln Phe Ala Phe Tyr Leu Gly Asp Thr Asn Thr
 65                  70                  75                  80

Asn Glu Glu Asp Gly Gly Leu Ala Thr Phe Gly Gly Val Asp Glu Ser
                 85                  90                  95

Lys Tyr Thr Gly Lys Val Thr Trp Leu Pro Val Arg Arg Lys Ala Tyr
            100                 105                 110

Trp Glu Val Ser Leu Asp Gly Ile Ser Leu Gly Asp Glu Tyr Ala Pro
        115                 120                 125

Leu Glu Gly His Gly Ala Ala Ile Asp Thr Gly Thr
    130                 135                 140
```

<210> SEQ ID NO 14
<211> LENGTH: 17

```
<212> TYPE: DNA
<213> ORGANISM: Artificial Sequence
<220> FEATURE:
<223> OTHER INFORMATION: Oligonucleotide primer

<400> SEQUENCE: 14
atgtcaacac atttacc                                                        17

<210> SEQ ID NO 15
<211> LENGTH: 17
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)...(17)
<223> OTHER INFORMATION: n = A,T,C or G

<400> SEQUENCE: 15
cayggnacnc aytgygc                                                        17

<210> SEQ ID NO 16
<211> LENGTH: 368
<212> TYPE: DNA
<213> ORGANISM: Pichia methanolica
<220> FEATURE:
<221> NAME/KEY: CDS
<222> LOCATION: (1)...(366)
<221> NAME/KEY: misc_feature
<222> LOCATION: (1)...(368)
<223> OTHER INFORMATION: n = A,T,C or G

<400> SEQUENCE: 16 ggg tcc gna cnc atg gtg ttt cta aga att gcc cac att gtt gcc gtc            48
Gly Ser Xaa Xaa Met Val Phe Leu Arg Ile Ala His Ile Val Ala Val
 1               5                  10                  15 aaa gtt tta aga tct aac ggt tca ggt tct atg ccc gat gtt gtc aag            96
Lys Val Leu Arg Ser Asn Gly Ser Gly Ser Met Pro Asp Val Val Lys
            20                  25                  30 ggt gtt gaa tat gct ccc aat gct cac ctt gcg gaa gcc aag gct aac           144
Gly Val Glu Tyr Ala Pro Asn Ala His Leu Ala Glu Ala Lys Ala Asn
        35                  40                  45 aag agt ggt ttt aaa ggt tct acc gcg aac atg tca tta ggt ggt ggt           192
Lys Ser Gly Phe Lys Gly Ser Thr Ala Asn Met Ser Leu Gly Gly Gly
    50                  55                  60 aaa tct cca gct tta gat atg tct gtt aac gct cct gtt aaa gca ggt           240
Lys Ser Pro Ala Leu Asp Met Ser Val Asn Ala Pro Val Lys Ala Gly
65                  70                  75                  80 tta cac ttt gcc gtt acc gct ggt aac gat aac act gat gca tgt aac           288
Leu His Phe Ala Val Thr Ala Gly Asn Asp Asn Thr Asp Ala Cys Asn
                85                  90                  95 tat tct cca gcc act act gaa aat act gtc act gtt gtt gct tcc act           336
Tyr Ser Pro Ala Thr Thr Glu Asn Thr Val Thr Val Val Ala Ser Thr
            100                 105                 110 tta tct gat tcg aga gct gac atg tct aac tc                                368
Leu Ser Asp Ser Arg Ala Asp Met Ser Asn
            115                 120

<210> SEQ ID NO 17
<211> LENGTH: 122
<212> TYPE: PRT
<213> ORGANISM: Pichia methanolica
<220> FEATURE:
<221> NAME/KEY: VARIANT
<222> LOCATION: (1)...(122)
```

<223> OTHER INFORMATION: Xaa = Any Amino Acid

<400> SEQUENCE: 17

```
Gly Ser Xaa Xaa Met Val Phe Leu Arg Ile Ala His Ile Val Ala Val
 1               5                  10                  15
Lys Val Leu Arg Ser Asn Gly Ser Gly Ser Met Pro Asp Val Val Lys
             20                  25                  30
Gly Val Glu Tyr Ala Pro Asn Ala His Leu Ala Glu Ala Lys Ala Asn
         35                  40                  45
Lys Ser Gly Phe Lys Gly Ser Thr Ala Asn Met Ser Leu Gly Gly Gly
 50                  55                  60
Lys Ser Pro Ala Leu Asp Met Ser Val Asn Ala Pro Val Lys Ala Gly
65                  70                  75                  80
Leu His Phe Ala Val Thr Ala Gly Asn Asp Asn Thr Asp Ala Cys Asn
                 85                  90                  95
Tyr Ser Pro Ala Thr Thr Glu Asn Thr Val Thr Val Val Ala Ser Thr
                100                 105                 110
Leu Ser Asp Ser Arg Ala Asp Met Ser Asn
            115                 120
```

<210> SEQ ID NO 18
<211> LENGTH: 17
<212> TYPE: DNA
<213> ORGANISM: Artificial Sequence
<220> FEATURE:
<223> OTHER INFORMATION: Oligonucleotide primer

<400> SEQUENCE: 18
taacaatttc acacagg                                                    17

<210> SEQ ID NO 19
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 19
cgttgtaaaa cgacggcc                                                   18

<210> SEQ ID NO 20
<211> LENGTH: 48
<212> TYPE: DNA
<213> ORGANISM: Artificial Sequence
<220> FEATURE:
<223> OTHER INFORMATION: Oligonucleotide primer

<400> SEQUENCE: 20
tcgatggatc cggaattcgt taaataaaac ttctaaagcc agttaaaa                  48

<210> SEQ ID NO 21
<211> LENGTH: 33
<212> TYPE: DNA
<213> ORGANISM: Artificial Sequence
<220> FEATURE:
<223> OTHER INFORMATION: Oligonucleotide primer

<400> SEQUENCE: 21
ctagcaagat ctccggggga tcgggtagtg aa                                   33

<210> SEQ ID NO 22
<211> LENGTH: 22

```
-continued

<212> TYPE: DNA
<213> ORGANISM: Artificial Sequence
<220> FEATURE:
<223> OTHER INFORMATION: Oligonucleotide primer

<400> SEQUENCE: 22
ccaactataa cttttaactg gc                                              22

<210> SEQ ID NO 23
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 23
aaaagatatc caactacatg                                                 20
```

PROTEASE-DEFICIENT STRAINS OF *PICHIA METHANOLICA*

CROSS-REFERENCE TO RELATED APPLICATIONS

This application is a continuation-in-part of application Ser. No. 09/152,180, filed Sep. 11, 1998, which application is pending and which claims the benefit under 35 U.S.C. § 119(e) of provisional application 60/058,822, filed Sep. 15, 1997; and of application Ser. No. 08/703,807, filed Aug. 26, 1996, which application is pending and which claims the benefit under 35 U.S.C. § 119(e) of provisional applications 60/042,910, filed Jul. 17, 1996, and 60/006,397, filed Nov. 9, 1995.

BACKGROUND OF THE INVENTION

Methylotrophic yeasts are those yeasts that are able to utilize methanol as a sole source of carbon and energy. Species of yeasts that have the biochemical pathways necessary for methanol utilization are classified in four genera, Hansenula, Pichia, Candida, and Torulopsis. These genera are somewhat artificial, having been based on cell morphology and growth characteristics, and do not reflect close genetic relationships (Billon-Grand, *Mycotaxon* 35:201–204, 1989; Kurtzman, *Mycologia* 84:72–76, 1992). Furthermore, not all species within these genera are capable of utilizing methanol as a source of carbon and energy. As a consequence of this classification, there are great differences in physiology and metabolism between individual species of a genus.

Methylotrophic yeasts are attractive candidates for use in recombinant protein production systems. Some methylotrophic yeasts have been shown to grow rapidly to high biomass on minimal defined media. Certain genes of methylotrophic yeasts are tightly regulated and highly expressed under induced or de-repressed conditions, suggesting that promoters of these genes might be useful for producing polypeptides of commercial value. See, for example, Faber et al., *Yeast* 11:1331, 1995; Romanos et al., *Yeast* 8:423, 1992; and Cregg et al., *Bio/Technology* 11:905, 1993.

Development of methylotrophic yeasts as hosts for use in recombinant production systems has been slow, due in part to a lack of suitable materials (e.g., promoters, selectable markers, and mutant host cells) and methods (e.g., transformation techniques). The most highly developed methylotrophic host systems utilize *Pichia pastoris* and *Hansenula polymorpha* (Faber et al., *Curr. Genet.* 25:305–310, 1994; Cregg et al., ibid.; Romanos et al., ibid.; U.S. Pat. No. 4,855,242; U.S. Pat. No. 4,857,467; U.S. Pat. No. 4,879,231; and U.S. Pat. No. 4,929,555).

Minimization of spurious proteolysis of recombinant proteins generated under high cell density fermentation conditions is highly desirable. In yeast, the major store of proteolytic activity is located within the lumen of the vacuolar compartment (Jones, *Methods Enzymol.* 194:428–453, 1991). These proteases are released into the fermentation broth by spontaneous and inevitable cell lysis and are further liberated during cell breakage that is required to release intracellulary produced proteins in laboratory or industrial production. Although vacuolar proteases are required for several developmental transitions in the life cycle of yeast cells (e.g., sporulation), they are dispensible for vegetative growth. The majority of vacuolar proteases are synthesized and transported through the secretory pathway as enzymatically inactive zymogens (Klionsky et al., *Microbiol. Rev.* 54:266–292, 1990; Raymond et al., *Int. Rev. Cytol.* 139:59–120, 1992). They are proteolytically activated by the combined action of proteinase A, the product of the PEP4 gene, and proteinase B, the product of the PRB1 gene; hence pep4 prb1 mutants are generally considered to be fully protease-deficient (Jones, ibid.). Although protease-deficient strains of several species of yeast have been described (e.g., Gleeson et al., U.S. Pat. No. 5,324,660; Jones, *Methods Enzymol.* 194:428–453, 1991; Fleer et al., WO 94/00579), protease-deficient strains of *P. methanolica* have not been available and methods for the generation of such strains have not heretofore been available.

There remains a need in the art for strains and techniques that will facilitate the commercial development of additional species of methylotrophic yeasts, including the use of *Pichia methanolica* to produce polypeptides of economic importance. The present invention provides such strains and techniques, as well as other, related advantages.

SUMMARY OF THE INVENTION

It is an object of the present invention to provide a *Pichia methanolica* cell having a functional deficiency in a vacuolar protease.

It is a further object of the invention to provide methods for generating a *Pichia methanolica* cell deficient in a vacuolar protease.

It is a further object of the invention to provide methods for producing proteins heterologous to *Pichia methanolica*.

Within one aspect of the invention there is provided a *Pichia methanolica* cell having a functional deficiency in a vacuolar protease, wherein the functional deficiency is a result of a genetic defect, wherein the defect is an insertion, deletion, or substitution of one or more base pairs in a parent gene, wherein the parent gene is a gene encoding proteinase A or a gene encoding proteinase B. Within certain embodiments of the invention, the parent gene is a proteinase A gene comprising a sequence of nucleotides as shown in SEQ ID NO:12. Within other embodiments, the parent gene is a proteinase B gene comprising a sequence of nucleotides as shown in SEQ ID NO:16. Within additional embodiments, the cell has a genetic defect in each of a parent gene encoding proteinase A and a parent gene encoding proteinase B. Within additional embodiments of the invention, the cell has a further genetic defect, such as a genetic defect in a gene required for methanol utilization or a genetic defect in a gene required for nucleotide or amino acid biosynthesis. Within a preferred embodiment, the cell is auxotrophic for adenine. The invention also provides a cell having a further genetic defect wherein the cell contains an integrated genetic element, wherein the element comprises a gene that complements the further genetic defect.

A related aspect of the invention provides a *Pichia methanolica* cell as disclosed above containing an integrated genetic element comprising the following operably linked elements: (a) a transcription promoter of a *P. methanolica* gene; (b) a DNA segment encoding a polypeptide heterologous to *P. methanolica*; (c) a transcription terminator of a *P. methanolica* gene; and (d) a selectable marker. Within one embodiment, the cell is auxotrophic for adenine and the selectable marker is a *P. methanolica* ADE2 gene. Within another embodiment, the transcription promoter is a promoter of a methanol-inducible *P. methanolica* gene.

Within another aspect of the invention there is provided a method for generating a *Pichia methanolica* cell deficient in a vacuolar protease, comprising mutating a parent gene of the cell, the parent gene encoding a vacuolar protease, to produce a functionally deficient mutated gene. Within one embodiment, the parent gene is a gene encoding proteinase A or a gene encoding proteinase B. Within another embodiment, the step of mutating comprises deleting a portion of the parent gene.

Within an additional aspect, the invention provides a method of producing a protein comprising culturing a *Pichia methanolica* cell having a functional deficiency in a vacuolar protease, wherein the cell comprises an expression unit comprising a DNA segment encoding a protein heterologous to *P. methanolica*, under conditions in which the DNA segment is expressed, and recovering the protein encoded by the DNA segment. Within certain embodiment of the invention, the functional deficiency is a result of a genetic defect, wherein the defect is an insertion, deletion, or substitution of one or more base pairs in a parent gene, wherein the parent gene is a gene encoding proteinase A or a gene encoding proteinase B. Within a further embodiment, the cell has a genetic defect in each of a parent gene encoding proteinase A and a parent gene encoding proteinase B. Within additional embodiments of the invention, the cell has a further genetic defect, such as a genetic defect in a gene required for methanol utilization or a genetic defect in a gene required for nucleotide or amino acid biosynthesis. Within a preferred embodiment, the cell is auxotrophic for adenine.

Within another aspect, the invention provides a DNA construct comprising a *P. methanolica* gene segment, wherein the segment is selected from the group consisting of a segment comprising a sequence of nucleotides as shown in SEQ ID NO:12 and a segment comprising a sequence of nucleotides as shown in SEQ ID NO:16.

These and other aspects of the invention will become evident upon reference to the following detailed description and the attached drawings.

DETAILED DESCRIPTION OF THE INVENTION

Figure 1:
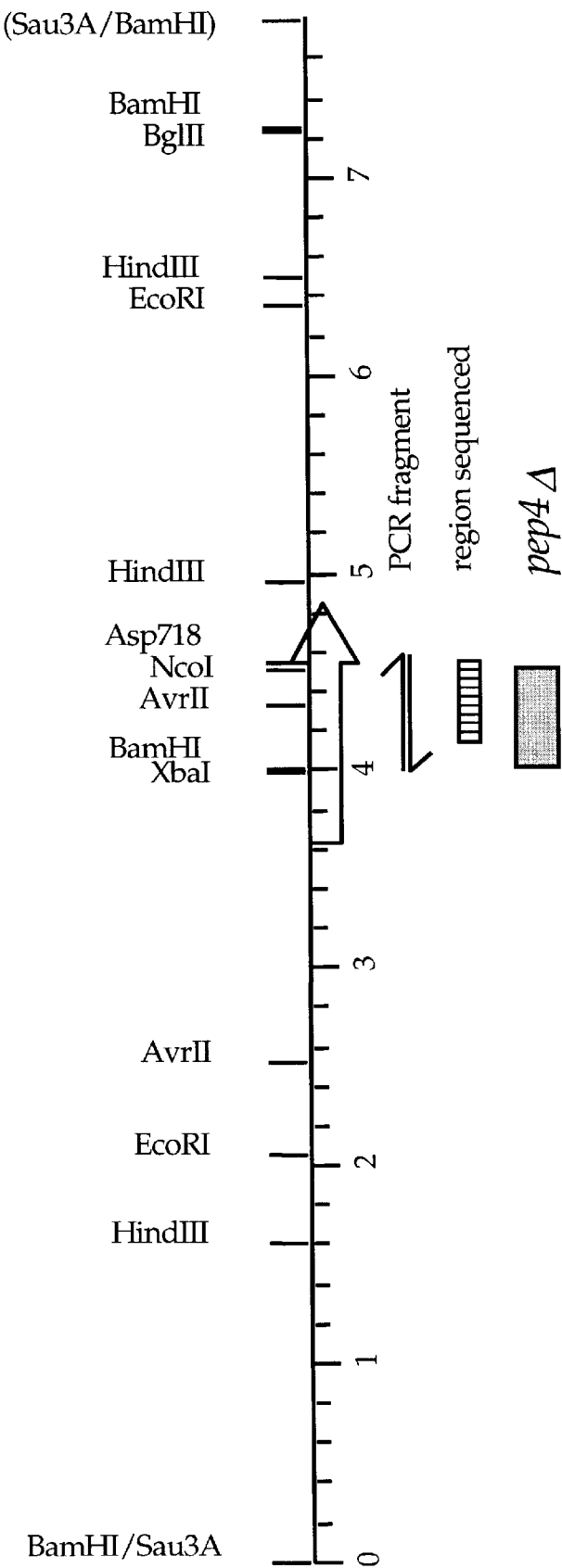
FIG. 1 shows a partial restriction map of a genomic clone comprising a *P. methanolica* PEP4 gene. The PCR product used to identify the gene is shown as complementary half arrows. A 420 bp fragment left of the Asp718 site was sequenced. The pep4Δ allele was created by deleting the indicated region between the BamHI and NcoI sites.

Prior to setting forth the invention in more detail, it will be useful to define certain terms used herein:

The term "allele" is used in its conventional sense to denote a naturally occuring alternative form of a gene or chromosomal locus. Allelic variation arises naturally through mutation, and may result in phenotypic polymorphism within populations. Gene mutations can be silent (no change in the encoded polypeptide), due to the degeneracy of the genetic code, or may encode polypeptides having altered amino acid sequence. Gene sequences disclosed herein are those of individual alleles. Those skilled in the art will recognized that other alleles are expected to exist, and such other alleles are within the scope of the invention.

A "DNA construct" is a DNA molecule, either single- or double-stranded, that has been modified through human intervention to contain segments of DNA combined and juxtaposed in an arrangement not existing in nature. DNA constructs used within the present invention will, in general, not exceed 50 kb in length.

"Early log phase growth" is that phase of cellular growth in culture when the cell concentration is from $2\times10^6$ cells/ml to $8\times10^6$ cells/ml.

A "functionally deficient mutated gene" is a mutated gene which, as a result of a mutation, encodes for the expression of less than 10% of the activity of the expression product of its wild-type counterpart. It is preferred that the functionally deficient gene encode for less than 1% of the activity of its wild-type counterpart, more preferably less than 0.01% as determined by appropriate assays. It is most preferred that the activity be essentially undetectable (i.e., not significantly above background). Functionally deficient genes can be generated by mutations in either coding or non-coding regions.

"Heterologous DNA" refers to a DNA molecule, or a population of DNA molecules, that does not exist naturally within a given host cell. DNA molecules heterologous to a particular host cell may contain DNA derived from the host cell species so long as that host DNA is combined with non-host DNA. For example, a DNA molecule containing a non-host DNA segment encoding a polypeptide operably linked to a host DNA segment comprising a transcription promoter is considered to be a heterologous DNA molecule.

A "higher eukaryotic" organism is a multicellular eukaryotic organism. The term encompasses both plants and animals.

An "integrated genetic element" is a segment of DNA that has been incorporated into a chromosome of a host cell after that element is introduced into the cell through human manipulation. Within the present invention, integrated genetic elements are most commonly derived from linearized plasmids that are introduced into the cells by electroporation or other techniques. Integrated genetic elements are passed from the original host cell to its progeny.

"Integrative transformants" are cells into which has been introduced heterologous DNA, wherein the heterologous DNA has become integrated into the genomic DNA of the cells.

"Linear DNA" denotes DNA molecules having free 5' and 3' ends, that is non-circular DNA molecules. Linear DNA can be prepared from closed circular DNA molecules, such as plasmids, by enzymatic digestion or physical disruption.

The term "operably linked" indicates that DNA segments are arranged so that they function in concert for their intended purposes, e.g., transcription initiates in the promoter and proceeds through the coding segment to the terminator.

The term "parent gene" is applied to a gene before it is mutagenized. The mutagenized gene will be altered in nucleotide sequence as compared to the parent gene. The mutagenized gene may also be either longer or shorter than the parent gene due to the insertion or deletion of one or more base pairs.

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes. Sequence elements within promoters that function in the initiation of transcription are often characterized by consensus nucleotide sequences. These promoter elements include RNA polymerase binding sites; TATA sequences; CAAT sequences; differentiation-specific elements (DSEs; McGehee et al., *Mol. Endocrinol.* 7:551–560, 1993); cyclic AMP response elements (CREs); serum response elements (SREs; Treisman, *Seminars in Cancer Biol.* 1:47–58, 1990); glucocorticoid response elements (GREs); and binding sites for other transcription factors, such as CRE/ATF (O'Reilly et al., *J. Biol. Chem.* 267:19938–19943, 1992), AP2 (Ye et al., *J. Biol. Chem.* 269:25728–25734, 1994), SP1, cAMP response element binding protein (CREB; Loeken, *Gene Expr.* 3:253–264, 1993) and octamer factors. See, in general, Watson et al., eds., *Molecular Biology of the Gene,* 4th ed., The Benjamin/Cummings Publishing Company, Inc., Menlo Park, Calif., 1987; and Lemaigre and Rousseau, *Biochem. J.* 303:1–14, 1994.

A "repressing carbon source" is a metabolizable, carbon-containing compound that, when not limited, suppresses the expression in an organism of genes required for the catablism of other carbon sources. By "limited" is meant that the carbon source is unavailable or becomes available at such a rate that it is immediately consumed and therefore the prevailing concentration of that carbon source in an organism's environment is effectively zero. Repressing carbon sources that can be used within the present invention include hexoses and ethanol. Glucose is particularly preferred.

"Rich" culture media are those culture media that are based on complex sources of nutrients, typically cell or tissue extracts or protein hydrolysates. Rich media will vary in composition from batch to batch due to variations in the composition of the nutrient sources.

"Vacuolar proteases" are defined by their function as those proteases that directly or indirectly provide the proteolytic activity present in the vacuole of a cell. The term is applied to proteases that are present in the vacuole, as well as to proteases that, through their proteolytic activity, cause the activation of proteases present in the vacuole.

The present invention provides protease-deficient strains of *Pichia methanolica* and methods for preparing such strains. Strains having a single such deficiency but exhibiting some vacuolar protease activity are useful intermediates in the generation of multiply mutant strains that are essentially free of vacuolar protease activity. Preferred deficient strains are those having functional deficiencies in the vacuolar proteases proteinase A, which is encoded by the PEP4 gene, and proteinase B, which is encoded by the PRB1 gene. Such deficiencies are created by mutations causing partial or complete loss of gene function. Within a preferred embodiment of the invention, the mutation results in structural change in one or more regions of the encoded protein that are required for activity. Mutations can be point mutations, more preferably insertions, and most preferably deletions of up to the entire open reading frame (the "ORF") of the target gene. Mutations spanning small regions (including point mutations, small insertions, and small deletions) will generally be directed to coding regions for structural motifs required for activity or will create frame shifts that eliminate protein activity. Those skilled in the art will recognize that, in addition to mutations within the ORF, mutations in untranslated regions of the gene can also reduce or negate gene function. When mutating untranslated sequences, it is preferred to target sequences within 1 kb of the ORF.

Strains of *Pichia methanolica* are available from the American Type Culture Collection (Rockville, Md.) and other repositories. These cells can be used within the present invention as parent strians for the production of protease-deficient strains. Those skilled in the art will recognize that parent and protease-deficient strains can be further mutagenized according to known techniques in order to obtain strains having desired genotypes. One can thereby obtain strains having defined nutritional requirements, metabolic defects, etc.

Vacuolar protease-deficient strains of *P. methanolica* can be constructed by a variety of genetic manipulations as disclosed above, any of which result in the reduction or lack of functional protease. It is preferred, however, to generate genetic defects by deleting a segment of the parent gene encoding the protease of interest. Such deletions will preferably eliminate one or more active site amino acid residues, thereby detroying proteolytic activity. Frameshift mutations, for example, can be generated by deleting a partial codon, thus deletion of a single nucleotide, and preferably at least four nucleotides, can produce the desired inactivating mutation. It is preferred, however, to delete most or all of the open reading frame of the parent gene, although in practice the actual extent of any deletion will be based on the locations of convenient restriction enzyme recognition sites. As noted above, vacuolar protease genes of particular interest in this regard include the PEP4 gene, which encodes proteinase A, and the PRB1 gene, which encodes proteinase B. The designations of these genes were based on functional equivalence to the *Saccharomyces cerevisiae* genes of the same names and by a high degree of sequence identity (70%) between the encoded *P. methanolica* and *S. cerevisiae* proteins. Although other vacuolar proteases (e.g., carboxypeptidase Y) are present in *P. methanolica*, the PEP4 and PRB1 gene products activate the other vacuolar proteases, so that negation of PEP4 and PRB1 functions results in a strain that is effectively vacuolar protease negative.

In contrast to other yeasts, including *S. cerevisiae* and *Pichia pastoris*, the PEP4 gene product of *P. methanolica* is not the dominant vacuolar proteolytic enzyme within this oraganism. *P. methanolica* pep4 mutants were not functionally deficient in vacuolar activity, whereas pep4 prb1 double mutants were. The data indicate that proteinase A autoactivates within the vacuole or a pre-vacuolar compartment, probably in response to low pH and the presence of $Ca^{++}$ and/or other ions. The activated enzyme then activates proteinase B, a non-specific proteinase which activates other vacuolar proteolytic enzymes. The data further indicate that proteinase B can be activated via alternative pathways.

A preferred method for creating a deletion within a vacuolar protease gene employs a loop-in/loop-out mutagenesis technique, whereby a disrupted copy of the protease gene is used to replace the endogenous copy within the genome. A deletion is created in a cloned vacuolar protease gene, typically by restriction endonuclease digestion and re-ligation or by the polymerase chain reaction (PCR; Mullis, U.S. Pat. No. 4,683,202). The disrupted copy of the gene is then introduced into the cell. It is preferred to utilize a linearized plasmid comprising, in addition to the disrupted protease gene, a selectable marker as disclosed in more detail below. The presence of the selectable marker facilitates the identification and selection of integrative transformants. Transformants that have undergone the desired homologous integration event are identified by Southern blotting (see, e.g., Strathern and Higgins, Methods Enzymol. 194:319–329, 1991). Genomic DNA is prepared from transformants and control cells, digested with one or more restriction enzymes, transferred to a blot, and probed to detect a change in the restriction pattern following transformation. Reagents, materials, equipment and protocols for preparing and probing blots are available from commercial suppliers.

Vacuolar protease activity (and therefore vacuolar protease deficiency) is measured using any of several known assays. Preferred assays are those developed for *Saccharomyces cerevisiae* and disclosed by Jones, *Methods Enzymol.* 194:428–453, 1991. A preferred such assay is the APE overlay assay, which detects activity of carboxypeptidase Y (CpY). Briefly, the assay detects the carboxypeptidase Y-mediated release of β-naphthol from an ester, which results in the formation of an isoluble red dye by the reaction of the β-naphthol with the diazonium salt Fast Garnet GBC. Colonies are overlayed with a 0.6% agar solution of N-Acetyl-DL-phenylalanine β-naphthyl ester containing 1 mg/ml dimethylformamide. After the overlay hardens, the plates are flooded with a solution of Fast Garnet GBC (5 mg/ml in 0.1 M Tris-HCl, pH 7.3–7.5). Within a few minutes, $Cpy^+$ colonies turn red. Carboxypeptidase Y activity can also be detected by the well test, in which cells are distributed into wells of a microtiter test plate and incubated in the presence of N-benzoyl-l-tyrosine p-nitroanilide (BTPNA) and dimethylformarnide. The cells are permeabilized by the dimethylformamide, and CpY in the cells cleaves the amide bond in the BTPNA to give the yellow product p-nitroaniline. Assays for CpY will detect any mutation that reduces protease activity so long as that activity ultimately results in the reduction of CpY activity. Proteinase B activity can be detected using an HPA overlay test, which detects the solubilization of Hide Powder Azure by proteinase B. Colonies producing the enzyme are surrounded by a clear halo, while deficient mutants remain covered. Carboxypeptidase S can be assayed using a well test that detects the release of leucine from carbobenzoxyglycyl-l-leucine. In the presence of l-amino-acid oxidase, $H_2O_2$ is produced by the oxidation of the free leucine. The $H_2O_2$ reacts with o-dianisidine dihydrochloride in the presence of peroxidase to produce oxidized dianisidine, which is dark brown. Additional assays are known and within the level of ordinary skill in the art to perform.

Cells to be transformed with heterologous DNA will have a mutation that can be complemented by a gene (a "selectable marker") on the heterologous DNA molecule. This selectable marker allows the transformed cells to grow under conditions in which untransformed cells cannot multiply ("selective conditions"). The general principles of selection are well known in the art. Commonly used selectable markers are genes that encode enzymes required for the synthesis of amino acids or nucleotides. Cells having mutations in these genes cannot grow in media lacking the specific amino acid or nucleotide unless the mutation is complemented by the selectable marker. Use of such "selective" culture media ensures the stable maintenance of the heterologous DNA within the host cell. A preferred selectable marker of this type for use in *Pichia methanolica* is a *P. methanolica* ADE2 gene, which encodes phosphoribosyl-5-aminoimidazole carboxylase (AIRC; EC 4.1.1.21). The ADE2 gene, when transformed into an ade2 host cell, allows the cell to grow in the absence of adenine. The coding strand of a representative *P. methanolica* ADE2 gene sequence is shown in SEQ ID NO:1. The sequence illustrated includes 1006 nucleotides of 5' non-coding sequence and 442 nucleotides of 3' non-coding sequence, with the initiation ATG codon at nucleotides 1007–1009. Within a preferred embodiment of the invention, a DNA segment comprising nucleotides 407–2851 is used as a selectable marker, although longer or shorter segments can be used as long as the coding portion is operably linked to promoter and terminator sequences. Those skilled in the art will recognize that this and other sequences provided herein represent single alleles of the respective genes, and that allelic variation is expected to exist. Any functional ADE2 allele can be used as a selectable marker. Other nutritional markers that can be used within the present invention include the *P. methanolica* ADE1, HIS3, and LEU2 genes, which allow for selection in the absence of adenine, histidine, and leucine, respectively. *P. methanolica* genes can be cloned on the basis of homology with their counterpart *Saccharomyces cerevisiae* genes. Heterologous genes, such as genes from other fungi, can also be used as selectable markers.

For large-scale, industrial processes where it is desirable to minimize the use of methanol, it is preferred to use host cells having a genetic defect in a gene required for methanol utilization. Such genes include the alcohol oxidase genes AUG1 and AUG2, as well as genes encoding catalase, formaldehyde dehydrogenase, formate dehydrogenase, dihydroxyacetone synthase, dihydroxyacetone kinase, fructose 1,6-bisphosphate aldolase, and fructose 1,6-bisphosphatase. It is particularly preferred to use cells in which both alcohol oxidase genes (AUG1 and AUG2) are deleted.

To prepare auxotrophic mutants of *P. methanolica*, cells are first exposed to mutagenizing conditions, i.e., environmental conditions that cause genetic mutations in the cells. Methods for mutagenizing cells are well known in the art and include chemical treatment, exposure to ultraviolet light, exposure to x-rays, and retroviral insertional mutagenesis. Chemical mutagens include ethylmethane sulfonate (EMS), N-methyl-N'-nitro-N-nitrosoguanidine, 2-methoxy-6-chloro-9-[3-(ethyl-2-chloroethyl)aminopropylamino] acridine 2HCl, 5-bromouracil, acridine, and aflatoxin. See Lawrence, *Methods Enzymol.* 194:273–281, 1991. The proportion of mutagenized cells obtained is a function of the strength or amount of mutagenizing agent to which the cells are exposed. A low level of mutagen produces a small proportion of mutant cells. Higher levels of mutagen produce a higher proportion of mutant cells, but also kill more cells. It is therefore necessary to balance mutagenesis with killing so that a reasonable number of mutant cells is obtained. Balancing is generally done empirically by exposing cells to different conditions to establish a killing curve. In general, the cells are exposed to mutagenizing conditions and cultured for one day, after which they are tested for viability according to standard assay methods. In general, it is preferred to use a level of mutagenesis that results in 20–50% mortality, although one skilled in the art will recognize that this value can be adjusted as necessary, for example if working with a very large number of cells.

Mutagenized cells are then cultured in a rich medium to allow mutations to become established and replicated in at least a portion of the cell population. This step allows cells in which the genome has been altered to replicate the mutation and pass it on to their progeny, thereby establishing the mutation within the population.

The cells are then transferred to a culture medium deficient in assimilable nitrogen so that cellular nitrogen stores are depleted. By "deficient in assimilable nitrogen" it is meant that the medium lacks an amount of nitrogen sufficient to support growth of the cells. Depletion of cellular nitrogen stores will generally require about 12 to 24 hours of incubation, with 16 hours being sufficient under common conditions. Following depletion of nitrogen stores, the cells are cultured in a defined culture medium comprising an inorganic nitrogen source and an amount of an antifungal antibiotic sufficient to kill growing P. methanolica cells. The antibiotic nystatin (mycostatin) is preferred. Preferred inorganic nitrogen sources are those comprising ammonium ions, such as ammonium sulfate. In general, the medium will contain 10–200 mM ammonium, preferably about 60 mM ammonium. Nystatin is included at a concentration of 0.1 to 100 mg/l, preferably 0.5 to 20 mg/L, more preferably about 2 mg/L (10 units/L). Treatment with nystatin is carried out for ten minutes to six hours, preferably about 1 hour. Those skilled in the art will recognize that the actual antibiotic concentration and exposure time required to kill prototrophic cells can be readily determined empirically, and certain adjustments may be necessary to compensate for variations in specific activity between individual batches of antibiotic. By depleting cellular nitrogen stores and then culturing the cells in a defined medium containing an inorganic nitrogen source and antibiotic, cells that are auxotrophic for amino acid or nucleotide biosynthesis remain alive because they cannot grow in the defined medium. Growing cells are killed by the antibiotic. Following the antibiotic treatment, the cells are transferred to a rich culture medium.

Auxotrophic mutations are confirmed and characterized by determining the nutrient requirements of the treated cells. Replica plating is commonly used for this determination. Cells are plated on both rich medium and media lacking specific nutrients. Cells that do not grow on particular plates are auxotrophic for the missing nutrient. Complementation analysis can be used for further characterization.

In the alternative, a dominant selectable marker is used, thereby obviating the need for mutant host cells. Dominant selectable markers are those that are able to provide a growth advantage to wild-type cells. Typical dominant selectable markers are genes that provide resistance to antibiotics, such as neomycin-type antibiotics (e.g., G418), hygromycin B, and bleomycin/phleomycin-type antibiotics (e.g., Zeocin™; available from Invitrogen Corporation, San Diego, Calif.). A preferred dominant selectable marker for use in P. methanolica is the Sh bla gene, which inhibits the activity of Zeocin™.

Heterologous DNA can be introduced into P. methanolica cells by any of several known methods, including lithium transformation (Hiep et al., Yeast 9:1189–1197, 1993; Tarutina and Tolstorukov, Abst. of the 15th International Specialized Symposium on Yeasts, Riga (U.S.S.R.), 1991, 137; Ito et al., J. Bacteriol. 153:163, 1983; Bogdanova et al., Yeast 11:343, 1995), spheroplast transformation (Beggs, Nature 275:104, 1978; Hinnen et al., Proc. Natl. Acad. Sci. USA 75:1929, 1978; Cregg et al., Mol. Cell. Biol. 5:3376, 1985), freeze-thaw polyethylene glycol transformation (Pichia Expression Kit Instruction Manual, Invitrogen Corp., San Diego, Calif., Cat. No. K1710-01), or electroporation, the latter being preferred. Electroporation is the process of using a pulsed electric field to transiently permeabilize cell membranes, allowing macromolecules, such as DNA, to pass into cells. Electroporation has been described for use with mammalian (e.g., Neumann et al., EMBO J. 1:841–845, 1982) and fungal (e.g., Meilhoc et al., Bio/Technology 8:223–227, 1990) host cells. However, the actual mechanism by which DNA is transferred into the cells is not well understood. For transformation of P. methanolica, it has been found that electroporation is surprisingly efficient when the cells are exposed to an exponentially decaying, pulsed electric field having a field strength of from 2.5 to 4.5 kV/cm and a time constant ($\tau$) of from 1 to 40 milliseconds. The time constant $\tau$ is defined as the time required for the initial peak voltage $V_0$ to drop to a value of $V_0/e$. The time constant can be calculated as the product of the total resistance and capacitance of the pulse circuit, i.e., $\tau=R\times C$. Typically, resistance and capacitance are either preset or may be selected by the user, depending on the electroporation equipment selected. In any event, the equipment is configured in accordance with the manufacturer's instructions to provide field strength and decay parameters as disclosed above. Electroporation equipment is available from commercial suppliers (e.g., BioRad Laboratories, Hercules, Calif.).

DNA molecules for use in transforming P. methanolica will commonly be prepared as double-stranded, circular plasmids, which are preferably linearized prior to transformation. For polypeptide or protein production, the DNA molecules will include, in addition to the selectable marker disclosed above, an expression casette comprising a transcription promoter, a DNA segment (e.g., a cDNA) encoding the polypeptide or protein of interest, and a transcription terminator. These elements are operably linked to provide for transcription of the DNA segment of interest. It is preferred that the promoter and terminator be that of a P. methanolica gene. Useful promoters include those from constitutive and methanol-inducible promoters. Promoter sequences are generally contained within 1.5 kb upstream of the coding sequence of a gene, often within 1 kb or less. In general, regulated promoters are larger than constitutive promoters due the presence of regulatory elements. Methanol-inducible promoters, which include both positive and negative regulatory elements, may extend more than 1 kb upstream from the initiation ATG. Promoters are identified by function and can be cloned according to known methods.

A particularly preferred methanol-inducible promoter is that of a P. methanolica alcohol utilization gene. A representative coding strand sequence of one such gene, AUG1, is shown in SEQ ID NO:2. Within SEQ ID NO:2, the initiation ATG codon is at nucleotides 1355–1357. Nucleotides 1–23 of SEQ ID NO:2 are non-AUG1 polylinker sequence. It is particularly preferred to utilize as a promoter a segment comprising nucleotides 24–1354 of SEQ ID NO:2, although additional upstream sequence can be included. P methanolica contains a second alcohol utilization gene, AUG2, the promoter of which can be used within the present invention. A partial DNA sequence of one AUG2 clone is shown in SEQ ID NO:9. AUG2 promoter segments used within the present invention will generally comprise nucleotides 91–169 of SEQ ID NO:9, although small truncations at the 3' end would not be expected to negate promoter function. Other useful promoters include those of the dihydroxyacetone synthase (DHAS), formate dehydrogenase (FMD), and catalase (CAT) genes. Genes encoding these enzymes from other species have been described, and their sequences are available (e.g., Janowicz et al., Nuc. Acids Res. 13:2043, 1985; Hollenberg and Janowicz, EPO publication 0 299 108; Didion and Roggenkamp, FEBS Lett. 303:113, 1992). Genes encoding these proteins can be cloned by using the known sequences as probes, or by aligning known sequences, designing primers based on the alignment, and amplifying P. methanolica DNA by the polymerase chain reaction (PCR).

Constitutive promoters are those that are not activated or inactivated by environmental conditions; they are always transcriptionally active. Preferred constitutive promoters for use within the present invention include those from glyceraldehyde-3-phosphate dehydrogenase, triose phosphate isomerase, and phosphoglycerate kinase genes of P.

*methanolica*. These genes can be cloned as disclosed above or by complementation in a host cell, such as a *Saccharomyces cerevisiae* cell, having a mutation in the counterpart gene. Mutants of this type are well known in the art. See, for example, Kawasaki and Fraenkel, *Biochem. Biophys. Res. Comm.* 108:1107–1112, 1982; McKnight et al., *Cell* 46:143–147, 1986; Aguilera and Zimmermann, *Mol. Gen. Genet.* 202:83–89,1986.

DNA constructs used within the present invention may further contain additional elements, such as an origin of replication and a selectable marker that allow amplification and maintenance of the DNA in an alternate host (e.g., *E. coli*). To facilitate integration of the DNA into the host chromosome, it is preferred to have the entire expression segment, comprising the promoter—gene of interest— terminator plus selectable marker, flanked at both ends by host DNA sequences. This is conveniently accomplished by including 3' untranslated DNA sequence at the downstream end of the expression segment and relying on the promoter sequence at the 5' end. When using linear DNA, the expression segment will be flanked by cleavage sites to allow for linearization of the molecule and separation of the expression segment from other sequences (e.g., a bacterial origin of replication and selectable marker). Preferred such cleavage sites are those that are recognized by restriction endonucleases that cut infrequently within a DNA sequence, such as those that recognize 8-base target sequences (e.g., Not I).

Proteins that can be produced in *P. methanolica* include proteins of industrial and pharmaceutical interest. Such proteins include higher eukaryotic proteins from plants and animals, particularly vertebrate animals such as mammals, although certain proteins from microorganisms are also of great value. Examples of proteins that can be prepared include enzymes such as lipases, cellulases, and proteases; enzyme inhibitors, including protease inhibitors; growth factors such as platelet derived growth factor, fibroblast growth factors, and epidermal growth factor; cytokines such as erythropoietin and thrombopoietin; and hormones such as insulin, leptin, and glucagon.

For protein production, *P. methanolica* cells are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors. A preferred culture medium is YEPD (Table 1). The cells may be passaged by dilution into fresh culture medium or stored for short periods on plates under refrigeration. For long-term storage, the cells are preferably kept in a 50% glycerol solution at −70° C.

TABLE 1

YEPD

2% D-glucose
2% Bacto ™ Peptone (Difco Laboratories, Detroit, MI)
1% Bacto ™ yeast extract (Difco Laboratories)
0.004% adenine
0.006% L-leucine
ADE D 0.056%-Ade-Trp-Thr powder
0.67% yeast nitrogen base without amino acids
2% D-glucose
0.5% 200X tryptophan, threonine solution
ADE DS 0.056%-Ade-Trp-Thr powder
0.67% yeast nitrogen base without amino acids TABLE 1-continued 2% D-glucose
0.5% 200X tryptophan, threonine solution
18.22% D-sorbitol
LEU D 0.052%-Leu-Trp-Thr powder
0.67% yeast nitrogen base without amino acids
2% D-glucose
0.5% 200X tryptophan, threonine solution
HIS D 0.052%-His-Trp-Thr powder
0.67% yeast nitrogen base without amino acids
2% D-glucose
0.5% 200X tryptophan, threonine solution
URA D 0.056%-Ura-Trp-Thr powder
0.67% yeast nitrogen base without amino acids
2% D-glucose
0.5% 200X tryptophan, threonine solution
URA DS 0.056%-Ura-Trp-Thr powder
0.67% yeast nitrogen base without amino acids
2% D-glucose
0.5% 200X tryptophan, threonine solution
18.22% D-sorbitol
-Leu-Trp-Thr powder powder made by combining 4.0 g adenine, 3.0 g arginine, 5.0 g aspartic acid, 2.0 g histidine, 6.0 g isoleucine, 4.0 g lysine, 2.0 g methionine, 6.0 g phenylalanine, 5.0 g serine, 5.0 g tyrosine, 4.0 g uracil, and 6.0 g valine (all L-amino acids)
-His-Trp-Thr powder powder made by combining 4.0 g adenine, 3.0 g arginine, 5.0 g aspartic acid, 6.0 g isoleucine, 8.0 g leucine, 4.0 g lysine, 2.0 g methionine, 6.0 g phenylalanine, 5.0 g serine, 5.0 g tyrosine, 4.0 g uracil, and 6.0 g valine (all L-amino acids)
-Ura-Trp-Thr powder powder made by combining 4.0 g adenine, 3.0 g arginine, 5.0 g aspartic acid, 2.0 g histidine, 6.0 g isoleucine, 8.0 g leucine, 4.0 g lysine, 2.0 g methionine, 6.0 g phenylalanine, 5.0 g serine, 5.0 g tyrosine, and 6.0 g valine (all L-amino acids)
-Ade-Trp-Thr powder powder made by combining 3.0 g arginine, 5.0 g aspartic acid, 2.0 g histidine, 6.0 g isoleucine, 8.0 g leucine, 4.0 g lysine, 2.0 g methionine, 6.0 g phenylalanine, 5.0 g serine, 5.0 g tyrosine, 4.0 g uracil, and 6.0 g valine (all L-amino acids)
200 X tryptophan, threonine solution 3.0% L-threonine, 0.8% L-tryptophan in $H_2O$
For plates, add 1.8% Bacto ™ agar (Difco Laboratories)

Electroporation of *P. methanolica* is preferably carried out on cells in early log phase growth. Cells are streaked to single colonies on solid media, preferably solid YEPD. After about 2 days of growth at 30° C., single colonies from a fresh plate are used to inoculate the desired volume of rich culture media (e.g., YEPD) to a cell density of about $5–10 \times 10^5$ cells/ml. Cells are incubated at about 25–35° C., preferably 30° C., with vigorous shaking, until they are in early log phase. The cells are then harvested, such as by centrifugation at 3000×g for 2–3 minutes, and resuspended. Cells are made electrocompetent by reducing disulfide bonds in the cell walls, equilibrating them in an ionic solution that is compatible with the electroporation conditions, and chilling them. Cells are typically made electrocompetent by incubating them in a buffered solution at pH 6–8 containing a reducing agent, such as dithiothreitol (DTT) or β-mercaptoethanol (BME), to reduce cell wall proteins to facilitate subsequent uptake of DNA. A preferred incubation buffer in this regard is a fresh solution of 50 mM potassium phosphate buffer, pH 7.5, containing 25 mM DTT. The cells are incubated in this buffer (typically using one-fifth the original culture volume) at about 30° C. for about 5 to 30 minutes, preferably about 15 minutes. The cells are then harvested and washed in a suitable electroporation buffer, which is used ice-cold. Suitable buffers in this regard include pH 6–8 solutions containing a weak buffer, divalent cations (e.g., $Mg^{++}$, $Ca^{++}$) and an osmotic stabilizer (e.g., a sugar). After washing, the cells are resuspended in a small volume of the buffer, at which time they are electrocompetent and can be used directly or aliquotted and stored frozen (preferably at −70° C.). A preferred electroporation buffer is STM (270 mM sucrose, 10 mM Tris, pH 7.5, 1 mM $MgCl_2$). Within a preferred protocol, the cells are subjected to two washes, first in the original culture volume of ice-cold buffer, then in one-half the original volume. Following the second wash, the cells are harvested and resuspended, typically using about 3–5 ml of buffer for an original culture volume of 200 ml.

Electroporation is carried out using a small volume of electrocompetent cells (typically about 100 $\mu$l) and up to one-tenth volume of linear DNA molecules. For example, 0.1 ml of cell suspension in a buffer not exceeding 50 mM in ionic strength is combined with 0.1–10 $\mu$g of DNA (vol.$\leq$10 $\mu$l). This mixture is placed in an ice-cold electroporation cuvette and subjected to a pulsed electric field of from 2.5 to 4.5 kV/cm, preferably about 3.75 kV/cm, and a time constant of from 1 to 40 milliseconds, preferably 10–30 milliseconds, more preferably 15–25 milliseconds, most preferably about 20 milliseconds, with exponential decay. The actual equipment settings used to achieve the desired pulse parameters will be determined by the equipment used. When using a BioRad (Hercules, Calif.) Gene Pulser™ electroporator with a 2 mm electroporation cuvette, resistance is set at 600 ohms or greater, preferably "infinite" resistance, and capacitance is set at 25 $\mu$F to obtain the desired field characteristics. After being pulsed, the cells are diluted approximately 10× into 1 ml of YEPD broth and incubated at 30° C. for one hour.

The cells are then harvested and plated on selective media. Within a preferred embodiment, the cells are washed once with a small volume (equal to the diluted volume of the electroporated cells) of 1× yeast nitrogen base (6.7 g/L yeast nitrogen base without amino acids; Difco Laboratories, Detroit, Mich.), and plated on minimal selective media. Cells having an ade2 mutation that have been transformed with an ADE2 selectable marker can be plated on a minimal medium that lacks adenine, such as ADE D (Table 1) or ADE DS (Table 1). In a typical procedure, 250 $\mu$l aliquots of cells are plated on 4 separate ADE D or ADE DS plates to select for $Ade^+$ cells.

*P. methanolica* recognizes certain infrequently occuring sequences, termed autonomously replicating sequences (ARS), as origins of DNA replication, and these sequences may fortuitously occur within a DNA molecule used for transformation, allowing the transforming DNA to be maintained extrachromosomally. However, integrative transformants are generally preferred for use in protein production systems. Integrative transformants have a profound growth advantage over ARS transformants on selective media containing sorbitol as a carbon source, thereby providing a method for selecting integrative transformants from among a population of transformed cells. ARS sequences have been found to exist in the ADE2 gene and, possibly, the AUG1 gene of *P. methanolica*. ade2 host cells of *Pichia methanolica* transformed with an ADE2 gene can thus become $Ade^+$ by at least two different modes. The ARS within the ADE2 gene allows unstable extrachromosomal maintenance of the transforming DNA (Hiep et al., *Yeast* 9:1189–1197, 1993). Colonies of such transformants are characterized by slower growth rates and pink color due to prolific generation of progeny that are $Ade^-$. Transforming DNA can also integrate into the host genome, giving rise to stable transformants that grow rapidly, are white, and that fail to give rise to detectable numbers of $Ade^-$ progeny. ADE D plates allow the most rapid growth of transformed cells, and unstable and stable transformants grow at roughly the same rates. After 3–5 days of incubation on ADE D plates at 30° C. stable transformant colonies are white and roughly twice the size of unstable, pink transformants. ADE DS plates are more selective for stable transformants, which form large ($\approx$5 mm) colonies in 5–7 days, while unstable (ARS-maintained) colonies are much smaller ($\approx$1 mm). The more selective ADE DS media is therefore preferred for the identification and selection of stable transformants. For some applications, such as the screening of genetically diverse libraries for rare combinations of genetic elements, it is sometimes desirable to screen large numbers of unstable transformants, which have been observed to outnumber stable transformants by a factor of roughly 100. In such cases, those skilled in the art will recognize the utility of plating transformant cells on less selective media, such as ADE D.

Integrative transformants are preferred for use in protein production processes. Such cells can be propagated without continuous selective pressure because DNA is rarely lost from the genome. Integration of DNA into the host chromosome can be confirmed by Southern blot analysis. Briefly, transformed and untransformed host DNA is digested with restriction endonucleases, separated by electrophoresis, blotted to a support membrane, and probed with appropriate host DNA segments. Differences in the patterns of fragments seen in untransformed and transformed cells are indicative of integrative transformation. Restriction enzymes and probes can be selected to identify transforming DNA segments (e.g., promoter, terminator, heterologous DNA, and selectable marker sequences) from among the genomic fragments.

Differences in expression levels of heterologous proteins can result from such factors as the site of integration and copy number of the expression cassette and differences in promoter activity among individual isolates. It is therefore advantageous to screen a number of isolates for expression level prior to selecting a production strain. A variety of suitable screening methods are available. For example, transformant colonies are grown on plates that are overlayed with membranes (e.g., nitrocellulose) that bind protein. Proteins are released from the cells by secretion or following lysis, and bind to the membrane. Bound protein can then be assayed using known methods, including immunoassays. More accurate analysis of expression levels can be obtained by culturing cells in liquid media and analyzing conditioned media or cell lysates, as appropriate. Methods for concentrating and purifying proteins from media and lysates will be determined in part by the protein of interest. Such methods are readily selected and practiced by the skilled practitioner.

For small-scale protein production (e.g., plate or shake flask production), *P. methanolica* transformants that carry an expression cassette comprising a methanol-regulated promoter (such as the AUG1 promoter) are grown in the presence of methanol and the absence of interfering amounts of other carbon sources (e.g., glucose). For small-scale experiments, including preliminary screening of expression levels, transformants may be grown at 30° C. on solid media containing, for example, 20 g/L Bacto-agar (Difco), 6.7 g/L yeast nitrogen base without amino acids (Difco), 10 g/L methanol, 0.4 μg/L biotin, and 0.56 g/L of -Ade-Thr-Trp powder. Because methanol is a volatile carbon source it is readily lost on prolonged incubation. A continuous supply of methanol can be provided by placing a solution of 50% methanol in water in the lids of inverted plates, whereby the methanol is transferred to the growing cells by evaporative transfer. In general, not more than 1 mL of methanol is used per 100-mm plate. Slightly larger scale experiments can be carried out using cultures grown in shake flasks. In a typical procedure, cells are cultivated for two days on minimal methanol plates as disclosed above at 30° C., then colonies are used to inoculate a small volume of minimal methanol media (6.7 g/L yeast nitrogen base without amino acids, 10 g/L methanol, 0.4 μg/L biotin) at a cell density of about $1 \times 10^6$ cells/ml. Cells are grown at 30° C. Cells growing on methanol have a high oxygen requirement, necessitating vigorous shaking during cultivation. Methanol is replenished daily (typically 1/100 volume of 50% methanol per day).

For production scale culturing, fresh cultures of high producer clones are prepared in shake flasks. The resulting cultures are then used to inoculate culture medium in a fermenter. Typically, a 500 ml culture in YEPD grown at 30° C. for 1–2 days with vigorous agitation is used to inoculate a 5-liter fermenter. The cells are grown in a suitable medium containing salts, glucose, biotin, and trace elements at 28° C., pH 5.0, and >30% dissolved $O_2$. After the initial charge of glucose is consumed (as indicated by a decrease in oxygen consumption), a glucose/methanol feed is delivered into the vessel to induce production of the protein of interest. Because large-scale fermentation is carried out under conditions of limiting carbon, the presence of glucose in the feed does not repress the methanol-inducible promoter. The use of glucose in combination with methanol under glucose-limited conditions produces rapid growth, efficient conversion of carbon to biomass and rapid changes in physiological growth states, while still providing full induction of methanol-inducible gene promoters. In a typical fermentation run, a cell density of from about 80 to about 400 grams of wet cell paste per liter is obtained. "Wet cell paste" refers to the mass of cells obtained by harvesting the cells from the fermentor, typically by centrifugation of the culture.

The invention is further illustrated by the following non-limiting examples.

EXAMPLES

Example 1

*P. methanolica* cells (strain CBS6515 from American Type Culture Collection, Rockville, Md.) were mutagenized by UV exposure. A killing curve was first generated by plating cells onto several plates at approximately 200–250 cells/plate. The plates were then exposed to UV radiation using a G8T5 germicidal lamp (Sylvania) suspended 25 cm from the surfaces of the plates for periods of time as shown in Table 2. The plates were then protected from visible light sources and incubated at 30° C. for two days.

TABLE 2

| | Viable Cells | | |
|---|---|---|---|
| Time | Plate 1 | Plate 2 | Average |
| 0 sec. | 225 | 229 | 227 |
| 1 sec. | 200 | 247 | 223 |
| 2 sec. | 176 | 185 | 181 |
| 4 sec. | 149 | 86 | 118 |
| 8 sec. | 20 | 7 | 14 |
| 16 sec. | 0 | 2 | 1 |

Large-scale mutagenesis was then carried out using a 2-second UV exposure to provide about 20% killing. Cells were plated at approximately $10^4$ cells/plate onto eight YEPD plates that were supplemented with 100 mg/L each of uracil, adenine, and leucine, which were added to supplement the growth of potential auxotrophs having the cognate deficiencies. Following UV exposure the plates were wrapped in foil and incubated overnight at 30° C. The following day the colonies on the plates ($\sim 10^5$ total) were resuspended in water and washed once with water. An amount of cell suspension sufficient to give an $OD_{600}$ of 0.1–0.2 was used to inoculate 500 ml of minimal broth made with yeast nitrogen base without amino acids or ammonia, supplemented with 1% glucose and 400 μg/L biotin. The culture was placed in a 2.8 L baffled Bell flask and shaken vigorously overnight at 30° C. The following day the cells had reached an $OD_{600}$ of ~1.0–2.0. The cells were pelleted and resuspended in 500 ml of minimal broth supplemented with 5 g/L ammonium sulfate. The cell suspension was placed in a 2.8 L baffled Bell flask and shaken vigorously at 30° C. for 6 hours. 50 ml of the culture was set aside in a 250-ml flask as a control, and to the remainder of the culture was added 1 mg nystatin (Sigma Chemical Co., St. Louis, Mo.) to select for auxotrophic mutants (Snow, *Nature* 211:206–207, 1966). The cultures were incubated with shaking for an additional hour. The control and nystatin-treated cells were then harvested by centrifugation and washed with water three times. The washed cells were resuspended to an $OD_{600}$ of 1.0 in 50% glycerol and frozen. Titering of nystatin-treated cells versus the control cells for colony forming units revealed that nystatin enrichment had decreased the number of viable cells by a factor of $10^4$.

$10^{-2}$ dilutions of nystatin-treated cells were plated on 15 YEPD plates. Colonies were replica-plated onto minimal plates (2% agar, 1×YNB, 2% glucose, 400 μg/L biotin). The frequency of auxotrophs was about 2–4%. Approximately 180 auxotrophic colonies were picked to YEPD+Ade, Leu, Ura plates and replica-plated to various dropout plates. All of the auxotrophs were Ade⁻. Of these, 30 were noticeably pink on dropout plates (LEU D, HIS D, etc.; see Table 1). Of the 30 pink mutants, 21 were chosen for further study; the remainder were either leaky for growth on ADE D plates or contaminated with wild-type cells.

The Ade⁻ mutants were then subjected to complementation analysis and phenotypic testing. To determine the number of loci defined by the mutants, all 21 mutants were mated to a single pink, Ade⁻ tester strain (strain #2). Mating was carried out by mixing cell suspensions ($OD_{600}$=1) and plating the mixtures in 10 μl aliquots on YEPD plates. The cells were then replicated to SPOR media (0.5% Na acetate, 1% KCl, 1% glucose, 1% agar) and incubated overnight at 30° C. The cells were then replica-plated to ADE D plates for scoring of phenotype. As shown in Table 3, some combinations of mutants failed to give Ade⁺ colonies (possibly defining the same genetic locus as in strain #2), while others gave rise to numerous Ade+ colonies (possibly defining a separate genetic locus). Because mutant #3 gave Ade+ colonies when mated to #2, complementation testing was repeated with mutant #3. If the group of mutants defined two genetic loci, then all mutants that failed to give Ade+ colonies when mated to strain #2 should give Ade+ colonies when mated to #3. Results of the crosses are shown in Table 3.

TABLE 3

| Mutant | x Mutant #2 | x Mutant #3 |
| --- | --- | --- |
| #1 | + | − |
| #3 | + | − |
| #10 | + | − |
| #15 | + | − |
| #18 | + | − |
| #24 | + | − |
| #28 | + | − |
| #30 | + | − |
| #2 | − | + |
| #6 | − | + |
| #8 | − | + |
| #9 | − | + |
| #11 | − | + |
| #17 | − | + |
| #19 | − | + |
| #20 | − | + |
| #22 | − | + |
| #27 | − | + |
| #4 | + | + |
| #12 | + | + |
| #16 | + | + |

As shown in Table 3, most mutants fell into one of two groups, consistent with the idea that there are two adenine biosynthetic genes that, when missing, result in pink colonies on limiting adenine media. Three colonies (#4, #12, and #16) may either define a third locus or exhibit intragenic complementation. Two intensely pigmented mutants from each of the two complementation groups (#3 and #10; #6 and #11) were selected for further characterization. Additional analysis indicated that Ade− was the only auxotrophy present in these strains.

A *P. methanolica* clone bank was constructed in the vector pRS426, a shuttle vector comprising 2μ and *S. cerevisiae* URA3 sequences, allowing it to be propagated in *S. cerevisiae*. Genomic DNA was prepared from strain CBS6515 according to standard procedures. Briefly, cells were cultured overnight in rich media, spheroplasted with zymolyase, and lysed with SDS. DNA was precipitated from the lysate with ethanol and extracted with a phenol/chloroform mixture, then precipitated with ammonium acetate and ethanol. Gel electrophoresis of the DNA preparation showed the presence of intact, high molecular weight DNA and appreciable quantities of RNA. The DNA was partially digested with Sau 3A by incubating the DNA in the presence of a dilution series of the enzyme. Samples of the digests were analyzed by electrophoresis to determine the size distribution of fragments. DNA migrating between 4 and 12 kb was cut from the gel and extracted from the gel slice. The size-fractionated DNA was then ligated to pRS426 that had been digested with Bam HI and treated with alkaline phosphatase. Aliquots of the reaction mixture were electroporated in *E. coli* MC1061 cells using a BioRad Gene Pulser™ device as recommended by the manufacturer.

The genomic library was used to transform *S. cerevisiae* strain HBY21A (ade2 ura3) by electroporation (Becker and Guarente, *Methods Enzymol.* 194:182–187, 1991). The cells were resuspended in 1.2 M sorbitol, and six 300-μl aliquots were plated onto ADE D, ADE DS, URA D and URA DS plates (Table 1). Plates were incubated at 30° C. for 4–5 days. No Ade+ colonies were recovered on the ADE D or ADE DS plates. Colonies from the URA D and URA DS plates were replica-plated to ADE D plates, and two closely spaced, white colonies were obtained. These colonies were restreaked and confirmed to be Ura+ and Ade+. These two strains, designated Ade1 and Ade6, were streaked onto media containing 5 FOA (5 fluoro orotic acid; Sikorski and Boeke, *Methods Enzymol.* 194:302–318). Ura− colonies were obtained, which were found to be Ade− upon replica plating. These results indicate that the Ade+ complementing activity is genetically linked to the plasmid-borne URA3 marker. Plasmids obtained from yeast strains Ade1 and Ade6 appeared to be identical by restriction mapping as described below. These genomic clones were designated pADE1-1 and pADE1-6, respectively.

Total DNA was isolated from the HBY21A transformants Ade1 and Ade6 and used to transform *E. coli* strain MC1061 to Amp$^R$. DNA was prepared from 2 Amp$^R$ colonies of Ade1 and 3 Amp$^R$ colonies of Ade6. The DNA was digested with Pst I, Sca 1, and Pst I+Sca I and analyzed by gel electrophoresis. All five isolates produced the same restriction pattern.

PCR primers were designed from the published sequence of the *P. methanolica* ADE2 gene (also known as ADEI; Hiep et al., *Yeast* 9:1251–1258, 1993). Primer ZC9080 (SEQ ID NO:3) was designed to prime at bases 406–429 of the ADE2 DNA (SEQ ID NO:1), and primer ZC9079 (SEQ ID NO:4) was designed to prime at bases 2852–2829. Both primers included tails to introduce Avr II and Spe I sites at each end of the amplified sequence. The predicted size of the resulting PCR fragment was 2450 bp.

PCR was carried out using plasmid DNA from the five putative ADE2 clones as template DNA. The 100 μl reaction mixtures contained 1× Taq PCR buffer (Boehringer Mannheim, Indianapolis, Ind.), 10–100 ng of plasmid DNA, 0.25 mM dNTPs, 100 pmol of each primer, and 1 μl Taq polymerase (Boehringer Mannheim). PCR was run for 30 cycles of 30 seconds at 94° C., 60 seconds at 50° C., and 120 seconds at 72° C. Each of the five putative ADE2 genomic clones yielded a PCR product of the expected size (2.4 kb). Restriction mapping of the DNA fragment from one reaction gave the expected size fragments when digested with Bgl II or Sal I.

The positive PCR reactions were pooled and digested with Spe I. Vector pRS426 was digested with Spe I and treated with calf intestinal phosphatase. Four μl of PCR fragment and 1 μl of vector DNA were combined in a 10 μl reaction mix using conventional ligation conditions. The ligated DNA was analyzed by gel electrophoresis. Spe I digests were analyzed to identify plasmids carrying a subclone of the ADE2 gene within pRS426. The correct plasmid was designated pCZR118.

Because the ADE2 gene in pCZR118 had been amplified by PCR, it was possible that mutations that disabled the functional character of the gene could have been generated. To test for such mutations, subclones with the desired insert were transformed singly into *Saccharomyces cerevisiae* strain HBY21A. Cells were made electrocompetent and transformed according to standard procedures. Transformants were plated on URA D and ADE D plates. Three phenotypic groups were identified. Clones 1, 2, 11, and 12 gave robust growth of many transformants on ADE D. The transformation frequency was comparable to the frequency of Ura+ transformants. Clones 6, 8, 10, and 14 also gave a high efficiency of transformation to both Ura+ and Ade+, but the Ade+ colonies were somewhat smaller than those in the first group. Clone 3 gave many Ura+ colonies, but no Ade+ colonies, suggesting it carried a non-functional ade2 mutation. Clones 1, 2, 11, and 12 were pooled.

To identify the *P. methanolica* ade2 complementation group, two representative mutants from each complementation group (#3 and #10; #6 and #11), which were selected on the basis of deep red pigmentation when grown on limiting adenine, were transformed with the cloned ADE gene. Two hundred ml cultures of early log phase cells were harvested by centrifugation at 3000×g for 3 minutes and resuspended in 20 ml of fresh KD buffer (50 mM potassium phosphate buffer, pH 7.5, containing 25 mM DTT). The cells were incubated in this buffer at 30° C. for 15 minutes. The cells were then harvested and resuspended in 200 ml of ice-cold STM (270 mM sucrose, 10 mM Tris, pH 7.5, 1 mM $MgCl_2$). The cells were harvested and resuspended in 100 ml of ice-cold STM. The cells were again harvested and resuspended in 3–5 ml of ice-cold STM. 100-$\mu$l aliquouts of electrocompetent cells from each culture were then mixed with Not I-digested pADE1-1 DNA. The cell/DNA mixture was placed in a 2 mm electroporation cuvette and subjected to a pulsed electric field of 5 kV/cm using a BioRad Gene Pulser™ set to 1000$\Omega$ resistance and capacitance of 25 $\mu$F. After being pulsed, the cells were diluted by addition of 1 ml YEPD and incubated at 30° C. for one hour. The cells were then harvested by gentle centrifugation and resuspended in 400 $\mu$l minimal selective media lacking adenine (ADE D). The resuspended samples were split into 200-$\mu$l aliqouts and plated onto ADE D and ADE DS plates. Plates were incubated at 30° C. for 4–5 days. Mutants #6 and #11 gave Ade+ transformants. No Ade+ transformants were observed when DNA was omitted, hence the two isolates appeared to define the ade2 complementation group. The ADE2 sequence is shown in SEQ ID NO: 1.

Example 2

The *P. methanolica* clone bank disclosed in Example 1 was used as a source for cloning the Alcohol Utilization Gene (AUG1). The clone bank was stored as independent pools, each representing about 200–250 individual genomic clones. 0.1 $\mu$l of "miniprep" DNA from each pool was used as a template in a polymerase chain reaction with PCR primers (ZC8784, SEQ ID NO:5; ZC8787, SEQ ID NO:6) that were designed from an alignment of conserved sequences in alcohol oxidase genes from *Hansenula polymorpha*, *Candida boidini*, and *Pichia pastoris*. The amplification reaction was run for 30 cycles of 94° C., 30 seconds; 50° C., 30 seconds; 72° C., 60 seconds; followed by a 7 minute incubation at 72° C. One pool (#5) gave a ~600 bp band. DNA sequencing of this PCR product revealed that it encoded an amino acid sequence with ~70% sequence identity with the *Pichia pastoris* alcohol oxidase encoded by the AOX1 gene and about 85% sequence identity with the *Hansenula polymorpha* alcohol oxidase encoded by the MOX1 gene. The sequence of the cloned AUG1 gene is shown in SEQ ID NO:2.

Sub-pools of pool #5 were analyzed by PCR using the same primers used in the initial amplification. One positive sub-pool was further broken down to identify a positive colony. This positive colony was streaked on plates, and DNA was prepared from individual colonies. Three colonies gave identical patterns after digestion with Cla I.

Restriction mapping of the genomic clone and PCR product revealed that the AUG1 gene lay on a 7.5 kb genomic insert and that sites within the PCR fragment could be uniquely identified within the genomic insert. Because the orientation of the gene within the PCR fragment was known, the latter information provided the approximate location and direction of transcription of the AUG1 gene within the genomic insert. DNA sequencing within this region revealed a gene with very high sequence similarity at the amino acid level to other known alcohol oxidase genes.

Example 3

*P. methanolica* cells in which the AUG1 gene had been disrupted by insertion of a GAD65 expression construct retained the ability to grow on methanol, indicating that a second alcohol oxidase gene was present. The second gene, designated AUG2, was identified by PCR. Sequence analysis of the 5' coding region of the gene showed that the N-terminus of the encoded protein was similar to those of known alcohol oxidase genes.

Strain MC GAD8, a transformant that grew very poorly on minimal methanol broth, was used as a source for cloning the AUG2 gene. Genomic DNA was prepared from MC GAD8 and amplified with sense and antisense PCR primers specific for the AUG1 open reading frame (8784, SEQ ID NO:5; 8787, SEQ ID NO:6). A product identical in size to the AUG1 product but showing very low intensity on an analytical gel was obtained.

The putative AUG2 PCR product was digested with a battery of restriction enzymes. Partial digestion by Eco RI and Pvu I, and the presence of several Bgl II sites suggested that the DNA was contaminated with small amounts of AUG1. To remove the contaminating AUG1 DNA, the PCR mixture was cut with Eco RI and gel purified. Since the MC GAD 8 product did not appear to have an Eco RI site, it was unaffected. The resulting gel-purified DNA was reamplified and again analyzed by restriction digestion. The DNA gave a different restriction map from that of the AUGI PCR product.

Southern blot analysis was performed on genomic DNA from MC GAD8 and wild-type cells using either AUG1 or AUG2 open reading frame PCR fragments as probes. The AUG2 probe hybridized at low stringency to the AUG1 locus and at both low and high stringency to a second locus. The AUG1 probe bound to both loci at low stringency, but bound predominantly to the AUG1 locus at high stringency. These data indicated that the new PCR product from MC GAD8 was similar to but distinct from AUG1. Sequence analysis showed an 83% identity between AUG1 and AUG2 gene products.

To clone the AUG2 genomic locus, PCR primers were designed from the original AUG2 PCR fragment. Primers 9885 (SEQ ID NO:7) and 9883 (SEQ ID NO:8) were used to screen a *P. methanolica* genomic library. A positive clone bank pool was then probed with the original MC GAD8 PCR product. Cells were plated on 10 plates at about 5000 colonies/plate and grown overnight, then the plates were overlayed with filter discs (Hybond-N, Amersham Corp., Arlington Heights, Ill.). Colonies were denatured, neutralized, and UV cross-linked. Bacterial debris was washed from the filters with 5× SSC, and the filters were again cross-linked. Blots were pre-hybridized in pairs at 42° C. for 1 hour in 25 ml hybridization buffer. Approximately 250 ng of probe was then added to each pair of filters. Hybridization was conducted at 42° C. for four hours. The blots were then washed in 500 ml of 0.1×SSC, 6M urea, 0.4% SDS at 42° C. for 10 minutes, four times. The blots were then neutralized with 500 ml of 2×SSC at room temperature for 5 minutes, two rinses. The blots were then immersed in 100 ml development reagent (ECL, Amersham Corp.).

Positive colonies were picked and amplified using PCR primers 9885 (SEQ ID NO:7) and 9883 (SEQ ID NO:8) to confirm their identity. Positive pools were streaked on plates, and single colonies were rescreened by PCR. One colony was selected for further analysis (restriction mapping and sequencing). A partial sequence of the AUG2 gene is shown in SEQ ID NO:9. As shown in SEQ ID NO:9, the AUG2 sequence begins at the HindIII site a nucleotide 91. Nucleotides upstream from this position are vector sequence. The coding sequence begins at nucleotide 170.

Disruption of the AUG2 gene had little effect on cell growth on methanol. Cells lacking both functional AUG1 and AUG2 gene products did not grow on methanol. Subsequent analysis showed that the AUG1 gene product is the only detectable alcohol oxidase in cells grown in a fermentor.

Example 4

To generate a *P. methanolica* strain deficient for vacuolar proteases, the PEP4 and PRB1 genes were identified and disrupted. PEP4 and PRB1 sequences were amplified by PCR in reaction mixtures containing 100 pmol of primer DNA, 1x buffer as supplied (Boehringer Mannheim, Indianapolis, Ind.), 250 μM dNTPs, 1–100 pmol of template DNA, and 1 unit of Taq polymerase in a reaction volume of 100 μl. The DNA was amplified over 30 cycles of 94° C., 30 seconds; 50° C., 60 seconds; and 72° C., 60 seconds.

Using an alignment of PEP4 sequences derived from *S. cerevisiae* (Ammerer et al., *Mol. Cell. Biol.* 6:2490–2499, 1986; Woolford et al., *Mol. Cell. Biol.* 6:2500–2510, 1986) and *P. pastoris* (Gleeson et al., U.S. Pat. No. 5,324,660), several sense and antisense primers corresponding to conserved regions were designed. One primer set, ZC9118 (SEQ ID NO:10) and ZC9464 (SEQ ID NO:11) produced a PCR product of the expected size from genomic DNA, and this set was used to identify a genomic clone corresponding to the amplified region. DNA sequencing of a portion of this genomic clone (shown in SEQ ID NO:12) revealed an open reading frame encoding a polypeptide (SEQ ID NO:13) with 70% amino acid identity with proteinase A from *S. cerevisiae*.

Primers for the identification of *P. methanolica* PRB1 were designed on the basis of alignments between the PRB1 genes of *S. cerevisia* (Moehle et al., *Mol. Cell. Biol.* 7:4390–4399, 1987), *P. pastoris* (Gleeson et al., U.S. Pat. No. 5,324,660), and *Kluyveromyces lactis* (Fleer et al., WIPO Publication WO 94/00579). One primer set, ZC9126 (SEQ ID NO:14) and ZC9741 (SEQ ID NO:15) amplified a ca. 400 bp fragment from genomic DNA (SEQ ID NO:16). This product was sequenced and found to encode a polypeptide (SEQ ID NO:17) with 70% amino acid identity with proteinase B from *S. cerevisiae*. The PRB primer set was then used to identify a genomic clone encompassing the *P. methanolica* PRB1 gene.

Figure 2:
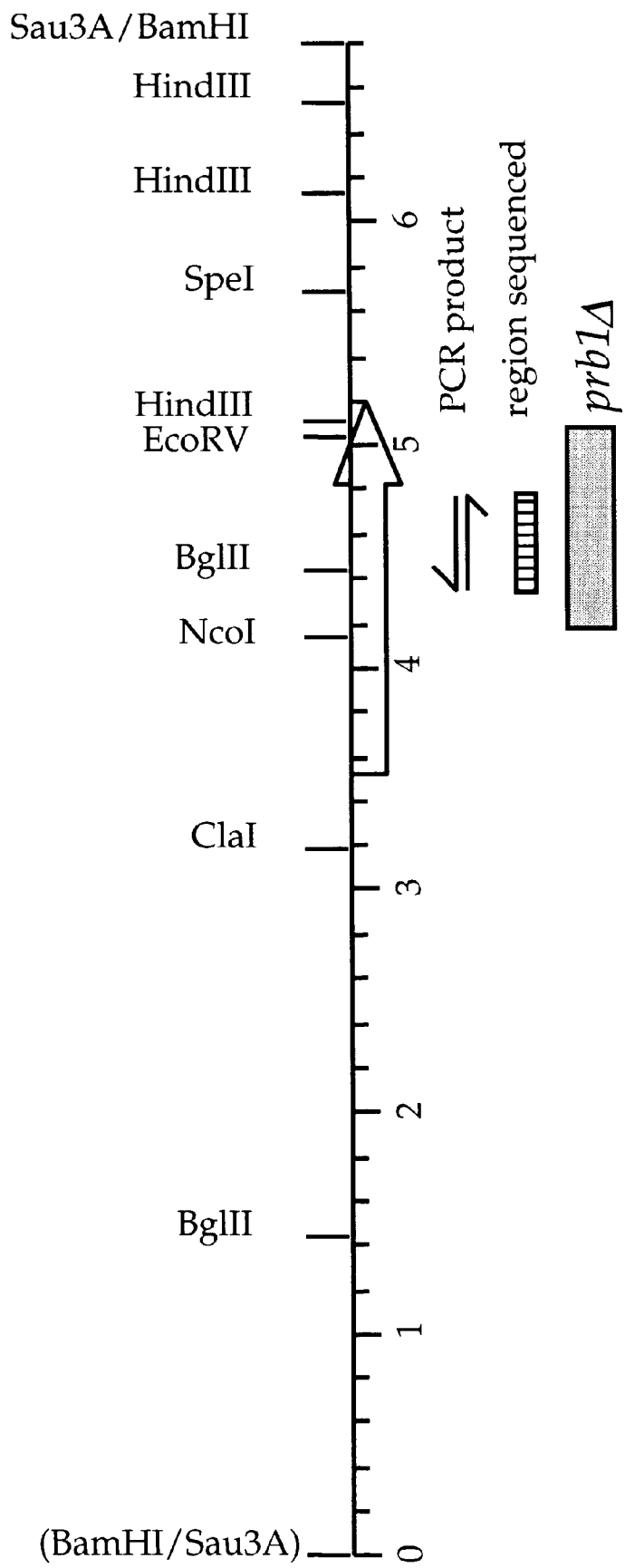
FIG. 2 shows a partial restriction map of a genomic clone comprising a *P. methanolica* PRB1 gene. The PCR product used to identify the gene is shown as complementary half arrows. The prb1Δ allele was generated by deleting the indicated region between the NcoI and EcoRV sites.

Deletion mutations in the *P. methanolica* PEP4 and PRB1 genes were generated using available restriction enzyme sites. The cloned genes were restriction mapped. The pep4Δ allele was created by deleting a region of approximately 500 bp between BamHI and NcoI sites (FIG. 1) and including nucleotides 1 through 393 the sequence shown in SEQ ID NO:12. The prb1Δ allele was generated by deleting a region of approximately 1 kbp between NcoI and EcoRV sites (FIG. 2) and including the sequence shown in SEQ ID NO:16. The cloned PEP4 and PRB1 genes were subcloned into pCZR139, a phagemid vector (pBluescript® II KS(+), Stratagene, La Jolla, Calif.) that carried a 2.4 kb SpeI ADE2 insert, to create the deletions. In the case of PEP4 gene, the unique BamHI site in pCZR139 was eliminated by digestion, fill-in, and religation. The vector was then linearized by digestion with EcoRI and HindIII, and a ca. 4 kb EcoRI-HindIII fragment spanning the PEP4 gene was ligated to the linearized vector to produce plasmid pCZR142. A ca. 500 bp deletion was then produced by digesting pCZR142 with BamHI and NcoI, filling in the ends, and religating the DNA to produce plasmid pCZR143. The PRB1 gene (~5 kb XhoI-BamHI fragment) was subcloned into pCZR139, and an internal EcoRV-NcoI fragment, comprising the sequence shown in SEQ ID NO:16, was deleted to produce plasmid pCZR153.

Plasmid pCZR143 was linearized with Asp718, which cut at a unique site. The linearized plasmid was introduced into the *P. methanolica* PMAD11 strain (an ade2 mutant generated as disclosed in Example 1). Transformants were grown on ADE DS (Table 1) to identify Ade$^+$ transformants. Two classes of white, Ade$^+$ transformants were analyzed. One class arose immediately on the primary transformation plate; the scond became evident as rapidly growing white papillae on the edges of unstable, pink transformant colonies.

Southern blotting was used to identify transformants that had undergone the desired homologous integration event. 100 μl of cell paste was scraped from a 24–48 hour YEPD plate and washed in 1 ml water. Washed cells were resuspended in 400 μl of spheroplast buffer (1.2 M sorbitol, 10 mM Na citrate pH 7.5, 10 mM EDTA, 10 mM DTT, 1 mg/ml zymolyase 100T) and incubated at 37° C. for 10 minutes. Four hundred μl of 1% SDS was added, the cell suspension was mixed at room temperature until clear, 300 μl of 5 M potassium acetate was mixed in, and the mixture was clarified by microcentrifugation for 5 minutes. 750 μl of the clarified lysate was extracted with an equal volume of phenol:chloroform:isoamyl alcohol (25:24:1), 600 μl was transferred to a fresh tube, 2 volumes of 100% ethanol was added, and the DNA was precipitated by microcentrifugation for 15 minutes at 4° C. The pellet was resuspended in 50 μl of TE (10 mM Tris pH 8.0, 1 mM EDTA) containing 100 μg/ml of RNAase A. Ten μl of DNA (approximately 100 ng) was digested in 100 μl total volume with appropriate enzymes, precipitated with 200 μl ethanol, and resuspended in 10 μl of DNA loading dye. The DNA was separated in 0.7% agarose gels and transferred to nylon membranes (Nytran N$^+$, Amersham Corp., Arlington Heights, Ill.) in a semi-dry blotting apparatus (BioRad Laboratories, Richmond, Calif.) as recommended by the manufacturer. Transferred DNA was denatured, neutralized, and cross-linked to the membrane with UV light using a Stratalinker (Stratagene, La Jolla, Calif.). To identify strains with a tandem integration at PEP4, two probes were used. One was a 1400 bp EcoRI-HindIII fragment from the 3' end of PEP4. The second was a 2000 bp BamHI-EcoRI fragment from the 5' end of PEP4. Fragments were detected using chemiluminescence reagents (ECL™ direct labelling kit; Amersham Corp., Arlington Heights, Ill.).

Parent strains harboring a tandem duplication of the wild-type and deletion alleles of the gene were grown in YEPD broth overnight to allow for the generation of looped-out, Ade$^{31}$ strains. These cells were then plated at a density of 2000–5000 colonies per plate on adenine-limited YEPD plates, grown for 3 days at 30° C. and 3 days at room temperature. The shift to room temperature enhanced pigmentation of rare, pink, Ade$^-$ colonies. Loop-out strains were consistently detected at a frequency of approximately one pink, Ade⁻ colony per 10,000 colonies screened. These strains were screened for retention of the wild-type or mutant genes by Southern blotting or by PCR using primers that spanned the site of the deletion. An ade2-11 pep4Δ strain was designated PMAD 15.

The PRB1 gene was then deleted from PMAD15 essentially as described above by transformation with plasmid pCZR153. Blots were probed with PCR-generated probes for internal portions of the PRB1 and ADE2 genes. The PRB1 probe was generated by subcloning a 2.6 kb ClaI-SpeI fragment of PRB1 into the phagemid vector pBluescript® II KS(+) to produce pCZR150, and amplifying the desired region by PCR using primers ZC447 (SEQ ID NO:18) and ZC976 (SEQ ID NO:19). The ADE2 probe was generated by amplifying the ADE2 gene in pCZR139 with primers ZC9079 (SEQ ID NO:4) and ZC9080 (SEQ ID NO:3). The resulting ade2-11 pep4Δ prb1Δ strain was designated PMAD16.

The effects of the pep4Δ and pep4Δ prb1Δ mutations on vacuolar protease activity were determined using the APNE overlay assay (Wolf and Fink, *J. Bacteriol.* 123:1150–1156, 1975; Jones, *Methods Enzymol.* 194:428–453, 1991). Protease proficient colonies become red upon addition of the overlay, while mutants devicient in vacuolar protease activity remain white. PMAD11 and PMAD15 colonies produced a bright red color. In contrast, colonies of PMAD16 remained white. While not wishing to be bound by theory, the Pep⁺ phenotype of the pep4Δ mutant may have been a consequence of phenotypic lag or the capability of the *P. methanolica* proteinase B for autoactivation. However, the pep4Δ prb1Δ strain possessed the desired protease-deficient phenotype.

Example 5

Figure 3:
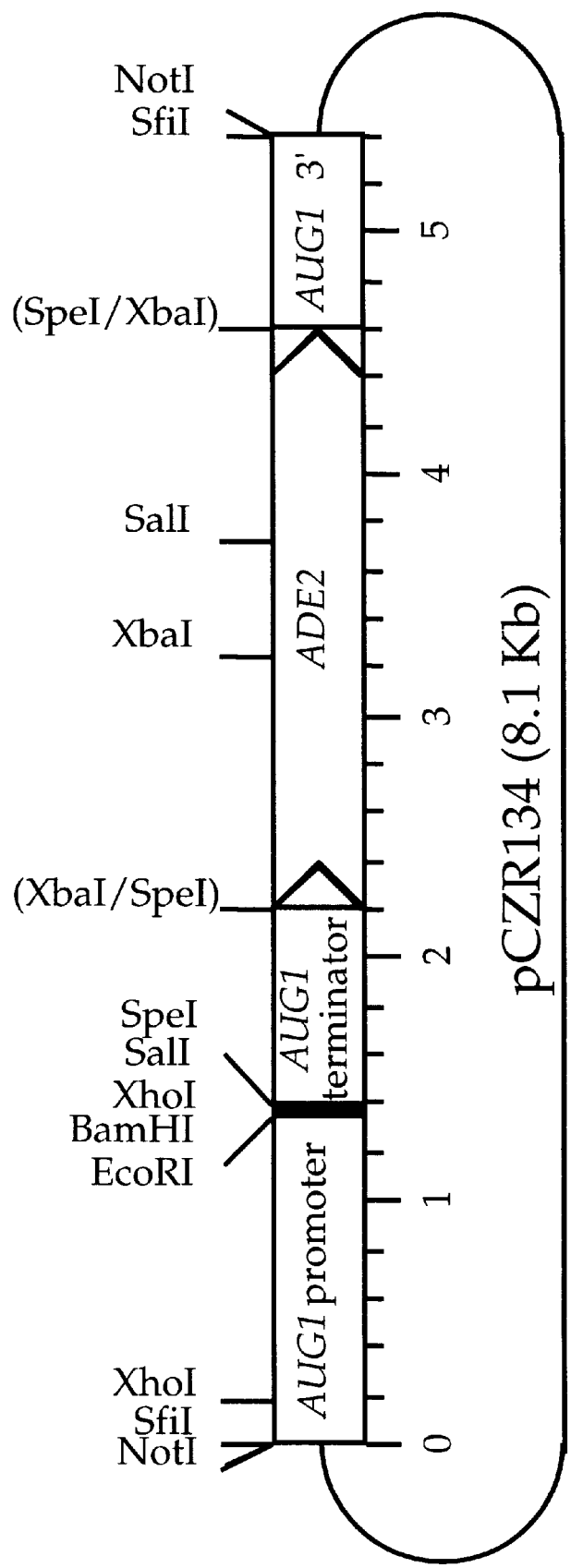
FIG. 3 illustrates the plasmid pCZR134.

A human glutamic acid decarboxylase (GAD$_{65}$) expression vector was constructed by inserting the cDNA encoding human GAD$_{65}$ (Karlsen et al., *Proc. Natl. Acad. Sci. USA* 88:8337–8341, 1991) as an EcoRI-XbaI fragment into the EcoRI-SpeI sites of plasmid pCZR134 (FIG. 3). The resulting expression vector, pCZR137, comprised the AUG1 promoter and terminator and ADE2 selectable marker.

Plasmid pCZR137 was digested with NotI and used to transform PMAD16 to Ade⁺. One thousand stable Ade⁺ transformants were screened for GAD$_{65}$ expression on minimal methanol plates using a nitrocellulose overlay, colony lysis and western blot technique essentially as disclosed by Wuestehube et al., *Genetics* 142:393–406, 1996. transformants were patched in grids of 50 to minimal plates lacking adenine, grown for 24 hours at 30° C., replica plated to minimal methanol plates, overlayed with nitrocellulose, and incubated for at least 48 hours at 30° C. Filters were removed from plates and placed colony side up for 30 minutes at room temperature on filter paper saturated with lysis buffer (0.1% SDS, 0.2 N NaOH, 35 mM DTT). Debris was rinsed from the filters under a stream of distilled water, and the filters were neutralized by a 5-minute incubation in 0.1 M acetic acid. The filters were then blocked in TTBS-NFM (20 mM Tris pH 7.4, 160 mM NaCl, 0.1% Tween 20, 5% non-fat milk) and incubated in TTBS-NFM containing the human GAD$_{65}$-specific monoclonal antibody GAD6 (Chang and Gottlieb, *J. Neurosci.* 8:2123–2130, 1988). Horseradish peroxidase-conjugated goat anti-mouse antibody was used to detect GAD65-specific immune complexes, which were visualized with commercially available chemiluminescence reagents (ECL™; Amersham Inc., Arlington Heights, Ill.) according to conventional techniques.

Ninety percent of the transformants were found to express GAD$_{65}$. Forty-six strains that appeared to express the highest levels of GAD$_{65}$ were reassayed by SDS-PAGE/western analysis. Forty-four of these strains appeared to make identical levels of GAD$_{65}$. Southern blot analysis (essentially as disclosed in Example 3) indicated that these strains carried a single copy of the GAD$_{65}$ expression cassette. Two strains appeared to make elevated levels of GAD$_{65}$. Both of these strains exhibited sluggish growth in minimal methanol broth, and analysis of genomic DNA from these strains by PCR using primers specific for AUG1 revealed that these strains were aug1Δ indicating that transplacement of the wild-type AUG1 gene by the GAD$_{65}$ expression cassette had occurred. The aug1 Δ strain making the highest apparent levels of GAD$_{65}$, PGAD4-2, was cultured under high cell density fermentation conditions in a BioFlow 3000 fermentor (New Brunswick Scientific Co., Inc., Edison, N.J.). An inoculum was generated by suspending cells from a 2-day YEPD plate in 250 ml of YEPD broth, and the culture was shaken vigorously overnight in a 1-liter baffled flask at 30° C. The fermentation vessel was charged with 2.5 liters of media containing 57.8 g (NH$_4$)$_2$SO$_4$, 46.6 g KCl, 30.8 g MgSO$_4$.7H$_2$O, 8.6 g CaSO$_4$.2H$_2$O, 2.0 g NaCl, and 10 ml of antifoam. After autoclaving and cooling of the vessel to a working temperature of 29° C., 350 ml of 50% glucose, 210 ml of 30% sodium hexametaphosphate (phosphate glass), and 250 ml of trace elements (containing, per liter, 27.8 g FeSO$_4$.7H$_2$O, 0.5 g CuSO$_4$.5H$_2$O, 1.09 g ZnCl$_2$, 1.35 g MnSO$_4$.H$_2$O, 0.48 g CoCl$_2$.6H$_2$O. 0.24 Na$_2$MoO$_4$2H$_2$O, 0.5 g H$_3$BO$_3$, 0.08 g KI, 5 mg biotin, 0.5 g thiamine, and 2.5 ml H$_2$SO$_4$) were added. The pH of the fermentor was adjusted to 5.0 and controlled automatically with 10% NH$_4$OH and 10% H$_3$PO$_4$. Aeration was provided initially as compressed air provided at a flow rate of 5 liters/minute and an impeller agitation rate of 300 rpm. After dissolved oxygen was set to 100%, the cell inoculum was added. Dissolved oxygen control was set to be maintained at 30% of saturation within and agitation range of 300–800 rpm. Oxygen demand above 800 rpm activated automatic supplementation with pure oxygen. The batch phase of growth was characterized by a steady increase in demand over a 24–36 hour period. Following exhaustion of glucose, the oxygen demand fell rapidly, and a glucose feed (containing, per 1.5 liter, 750 g glucose, 110 g (NH$_4$)$_2$SO$_4$, and 278 ml trace elements) was initiated at a rate of 0.4% glucose/hour. After 25 hours, the transtition to methanol induction of the AUG1 promoter was made with a mixed feed of glucose (0.2%/hour) and methanol (0.2%/hour) for 5 hours. A final mixed methanol feed (0.1% glucose/hour, 0.4% methanol/hour) was run for 25 hours. Robust GAD$_{65}$ expression was induced by the addition of methanol. The expression level of GAD$_{65}$ was calculated to be about 500 mg/L in a final cell mass of 170 grams wet cell paste/L.

Example 6

Figure 4:
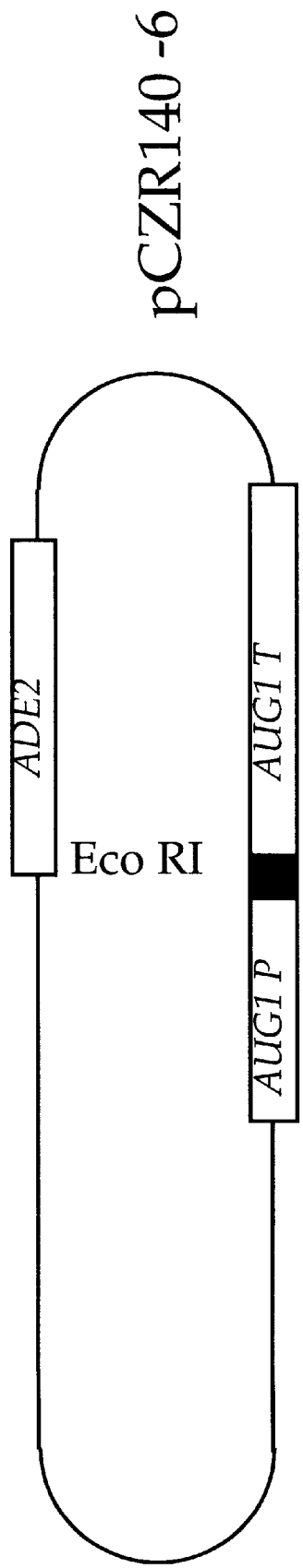
FIG. 4 illustrates the plasmid pCZR140-6.

A vacuolar protease deficient (pep4Δ prb1Δ) *P. methanolica* strain that is genetically deleted for the major alcohol oxidase (aug1Δ) was prepared from strain PMAD16 (ade2-11 pep4Δ prb1Δ). This strain was transformed to Ade⁺ with the AUG1 disruption plasmid pCZR140-6 that had been linearized with the restriction enzyme Asp718I. Plasmid pCZR140-6 is a Bluescript® (Stratagene Cloning Systems, La Jolla, Calif.)-based vector containing the *P. methanolica* ADE2 gene and a mutant of AUG1 in which the entire open reading frame between the promoter and terminator regions has been deleted (FIG. 4). Unstable Ade⁺ transformants (which arise by recirculization of the transforming DNA and subsequent episomal propagation of the plasmid due to the presence of an ARS in the ADE2 marker) were identified by slow growth and pink color on ADE DS medium. Cells which had integrated the circular episome by homologous recombination produced rapid growing, white papillae on the edges of slow growing, pink colonies.

Stable, Ade⁺ papillae of PMAD16 cells transformed with the pCZRI40-6 plasmid were isolated, and genomic DNA was prepared. The DNA was digested with EcoRI and subjected to Southern blot analysis. A probe corresponding to the AUG1 promoter region was generated by PCR using oligonucleotide primers ZC9081 (SEQ ID NO:20) and ZC9084 (SEQ ID NO:21) and, as primer, a plasmid containing the AUG1 promoter fragment of pCZR134. Probing of the blot revealed that 4 of 10 stable Ade⁺ papillae examined had undergone homologous recombination of the AUG1 disruption plasmid into the AUG1 promoter region. These four colonies were streaked onto multiple plates of a nonselective medium (YEPD) to allow the growth of both Ade⁺ and Ade⁻ colonies. (On YEPD, Ade⁻ colonies develop a pink color owing to adenine starvation and subsequent expression of the ade2 (pink) phenotype. The integrated AUG1 disruption plasmid spontaneously undergoes mitotic homologous recombination, effectively looping the plasmid out of the genome. These 'loop-out' cells can be detected because they develop into pink colonies on nonselective media. Looping out of the aug1Δ disruption plasmid either restores the wild-type AUG1 allele or leaves the aug1Δ disruption allele in the AUG1 locus, depending on the site of recombination.) Ade⁻ loop-out colonies were screened by PCR using primers ZC10,635 (SEQ ID NO:22) and ZC14, 199 (SEQ ID NO:23) for aug1Δ disrupted strains. 10 of 15 strains screened yielded a 600 base pair PCR product, indicating that they had retained the aug1Δ allele. The remaining 5 strains screened yielded a 2.1 Kb AUG1 wild-type PCR product. Subsequent testing of growth on minimal methanol broth revealed that the 10 putative aug1Δ strains grew slowly in this medium while the 5 putative AUG1 cells grew well on this medium. This phenotype is characteristic of aug1$^D$ mutants. One of these colonies, isolate #3, was given the strain designation PMAD18.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A *Pichia methanolica* cell having a functional deficiency in a vacuolar protease, wherein said functional deficiency is a result of a genetic defect, wherein said defect is an insertion, deletion, or substitution of at least four contiguous base pairs in a parent gene, wherein said parent gene encodes proteinase A or proteinase B.

2. A *Pichia methanolica* cell according to claim 1 wherein said parent gene is a proteinase A gene as shown in SEQ ID NO:12.

3. A *Pichia methanolica* cell according to claim 1 wherein said parent gene is a proteinase B gene as shown in SEQ ID NO:16.

4. A *Pichia methanolica* cell according to claim 1 having a genetic defect in each of a parent gene encoding proteinase A and a parent gene encoding proteinase B.

5. A *Pichia methanolica* cell according to claim 4 wherein said proteinase A parent gene is a gene comprising a sequence of nucleotides as shown in SEQ ID NO:12 and wherein said proteinase B parent gene is a gene comprising a sequence of nucleotides as shown in SEQ ID NO:16.

6. A *Pichia methanolica* cell according to claim 1 wherein said genetic defect is a deletion.

7. A *Pichia methanolica* cell according to claim 1 further having a second genetic defect in a gene required for methanol utilization.

8. A *Pichia methanolica* cell according to claim 1 further having a second genetic defect in a gene required for nucleotide or amino acid biosynthesis.

9. A *Pichia methanolica* cell according to claim 8 wherein said cell is auxotrophic for adenine.

10. A *Pichia methanolica* cell according to claim 8 containing an integrated genetic element, wherein said element comprises a gene that complements said second genetic defect.

11. A *Pichia methanolica* cell according to claim 1 containing an integrated genetic element comprising the following operably linked elements:
  a transcription promoter of a *P. methanolica* gene;
  a DNA segment encoding a polypeptide heterologous to *P. methanolica*;
  a transcription terminator of a *P. methanolica* gene; and
  a selectable marker.

12. A *Pichia methanolica* cell according to claim 11 wherein said cell is auxotrophic for adenine and said selectable marker is a *P. methanolica* ADE2 gene.

13. A *Pichia methanolica* cell according to claim 11 wherein said transcription promoter is a promoter of a methanol-inducible *P. methanolica* gene.

14. A *Pichia methanolica* cell according to claim 13 wherein said methanol-inducible gene is an alcohol oxidase gene.

15. A method for generating a *Pichia methanolica* cell deficient in a vacuolar protease, comprising mutating a parent gene of said cell, said parent gene encoding proteinase A or proteinase B, to produce a functionally deficient mutated gene, wherein said deficiency is a result of a genetic defect, wherein said defect is an insertion, deletion, or substitution of at least four contiguous base pairs in said parent gene.

16. A method according to claim 15 wherein said parent gene is a gene encoding proteinase A of a gene encoding proteinase B.

17. A method according to claim 16 wherein said parent gene is a proteinase A gene as shown in SEQ ID NO:12.

18. A method according to claim 16 wherein said parent gene is a proteinase B gene as shown in SEQ ID NO:16.

19. A method according to claim 15 wherein said step of mutating comprises deleting a portion of said parent gene.

20. A method of producing a protein comprising:
  culturing a *Pichia methanolica* cell having a functional deficiency in a vacuolar protease, wherein said cell comprises an expression unit comprising a DNA segment encoding a protein heterologous to *P. methanolica*, under conditions in which said DNA segment is expressed; and
  recovering the protein encoded by the DNA segment, wherein said functional deficiency is a result of a genetic defect, wherein said defect is an insertion, deletion, or substitution of at least four contiguous base pairs in a parent gene, wherein said parent gene encodes proteinase A or proteinase B.

21. A method according to claim 20 wherein said parent gene is a proteinase A gene as shown in SEQ ID NO:12.

22. A method according to claim 20 wherein said parent gene is a proteinase B gene as shown in SEQ ID NO:16.

23. A method according to claim 20 wherein said cell has a genetic defect in each of a parent gene encoding proteinase A and a parent gene encoding proteinase B.

24. A method according to claim 22 wherein said proteinase A parent gene is a gene comprising a sequence of nucleotides as shown in SEQ ID NO:12 and wherein said proteinase B parent gene is a gene comprising a sequence of nucleotides as shown in SEQ ID NO:16.

25. A method according to claim 20 wherein said genetic defect is a deletion.

26. A method according to claim 20 wherein said cell further has a second genetic defect in a gene required for methanol utilization.

27. A method according to claim 20 wherein said cell further has a second genetic defect in a gene required for nucleotide or amino acid biosynthesis.

28. A method according to claim 27 wherein said cell is auxotrophic for adenine.

29. A method according to claim 27 wherein said cell contains a plasmid comprising a gene that complements said second genetic defect.

30. A DNA construct comprising a *P. methanolica* gene segment, said segment selected from the group consisting of:

(a) a segment comprising a sequence of nucleotides as shown in SEQ ID NO:12; and (b) a segment comprising a sequence of nucleotides as shown in SEQ ID NO:16.

31. A DNA construct comprising:

a *P. methanolica* gene encoding proteinase A or proteinase B from which at least 4 nucleotides have been deleted; and a gene that functions as a selectable marker in a *P. methanolica* host cell.

* * * * *